(12) United States Patent
Polavarapu et al.

(10) Patent No.: US 10,526,273 B2
(45) Date of Patent: Jan. 7, 2020

(54) SURFACE ACTIVE IONIC LIQUID WITH ACTIVITY IN AQUEOUS AND NON-AQUEOUS MEDIA

(71) Applicant: Vanderbilt University, Nashville, TN (US)

(72) Inventors: Prasad L. Polavarapu, Brentwood, TN (US); Vijay Raghavan, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 16/256,013

(22) Filed: Jan. 24, 2019

(65) Prior Publication Data

US 2019/0233363 A1     Aug. 1, 2019

Related U.S. Application Data

(60) Provisional application No. 62/621,216, filed on Jan. 24, 2018.

(51) Int. Cl.
| | |
|---|---|
| *C07C 69/34* | (2006.01) |
| *C07C 211/27* | (2006.01) |
| *C07C 69/67* | (2006.01) |
| *C07C 211/63* | (2006.01) |

(52) U.S. Cl.
CPC ............. *C07C 69/34* (2013.01); *C07C 69/67* (2013.01); *C07C 211/27* (2013.01); *C07B 2200/07* (2013.01); *C07C 211/63* (2013.01)

(58) Field of Classification Search
CPC .............................. C07C 211/27; C07C 69/34
See application file for complete search history.

(56) References Cited

FOREIGN PATENT DOCUMENTS

| WO | 9505154 A1 | 2/1995 |
| WO | 2015095051 A1 | 6/2015 |

OTHER PUBLICATIONS

Raghavan et al., "First room temperature chiral anionic liquid forming micelles and reverse micelles." The Journal of Physical Chemistry B. Feb. 8, 2017;121(7)1629-39.
National Center for Biotechnology Information. PubChem Identifier: CID=102218963, <https://pubchem.ncbi.nlm.nih.gov/compound/1022189> 2015, 8 pages.
National Center for Biotechnology Information. PubChem Identifier: CID=102218962, <https://pubchem.ncbi.nlm.nih.gov/compound/102218962> 2015, 9 pages.

*Primary Examiner* — Yevgeny Valenrod
*Assistant Examiner* — Blaine G Doletski
(74) *Attorney, Agent, or Firm* — Michael Best & Friedrich LLP

(57) ABSTRACT

Disclosed herein are surfactant compounds, that are surface active, liquid, chiral, and micelle forming. Also disclose herein are ionic liquids and compsitions comprising the surfactant compounds.

25 Claims, 22 Drawing Sheets

SURFACE ACTIVE IONIC LIQUID WITH ACTIVITY IN AQUEOUS AND NON-AQUEOUS MEDIA

CROSS-REFERENCE TO RELATED APPLICATIONS

This application claims priority to U.S. Provisional Application No. 62/621,216, filed Jan. 24, 2018, which is hereby incorporated by reference in its entirety.

STATEMENT OF GOVERNMENT INTEREST

This invention was made with government support under grant number CHE1464874 awarded by the National Science Foundation. The government has certain rights in the invention.

TECHNICAL FIELD

The present disclosure relates to surface active ionic liquid surfactants with detergent and stabilizing applications.

BACKGROUND

Very few known surfactants can form both micelles and reverse micelles; one widely used example being dioctylsulfosuccinate sodium salt (AOT). However, surfactants such as AOT are not liquids. They can crystallize and can cause effects that can be detrimental to various applications. AOT also possesses inferior physicochemical properties. Therefore, there remains a need for a surfactant that can form both micelles and reverse micelles with physiochemical properties better than AOT.

SUMMARY

Disclosed herein is a standalone ionic surfactant that is liquid (i.e. surface active ionic liquid, SAIL), chiral and can form micelles and reverse micelles.

In one aspect, disclosed are compounds of formula (I),

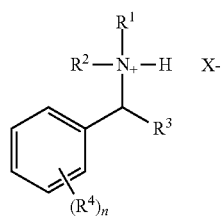

wherein
X— has formula (II)

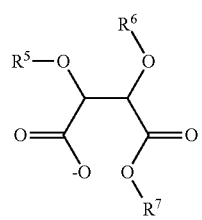

$R^1$ and $R^2$ are each independently hydrogen, $C_{1-4}$alkyl, $C_{3-4}$cycloalkyl, or —$CH_2$— cyclopropyl; or $R^1$ and $R^2$, taken together with the nitrogen to which they attach form a 4- to 7-membered saturated heterocycle;

$R^3$ is hydrogen, $C_{1-4}$alkyl, $C_{1-4}$haloalkyl, $C_{3-4}$cycloalkyl, —$CH_2$-cyclopropyl, or —$CH_2$—OH;

$R^4$ is halogen, cyano, $C_{1-4}$alkyl, $C_{1-4}$haloalkyl, OH, —$OC_{1-4}$alkyl, or —$OC_{1-4}$haloalkyl; wherein optionally two alkyl groups, taken together with the carbon atoms to which they attach form a 5- to 7-membered carbocyclic ring;

n is 0, 1, 2, 3, 4, or 5;

$R^5$ and $R^6$ are each independently hydrogen, —$C(O)C_{1-4}$alkyl, —$C(O)C_{3-4}$cycloalkyl, —$C(O)$—$CH_2$-cyclopropyl, $C_{1-4}$alkyl, or $C_{1-4}$haloalkyl; and $R^7$ is $C_{6-18}$alkyl optionally substituted with 1-6 halogen.

Also disclosed are ionic liquids and compositions comprising the compounds.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 5A shows the vibrational circular dichroism (VCD) (top) and vibrational absorption (bottom) spectra for 200 mM T12M in $D_2O$. FIG. 5B shows the electronic circular dichroism (ECD) (top) and electronic absorption (bottom) spectra for 10 and 200 mM T12M in $H_2O$.

DETAILED DESCRIPTION

Figure 1A:
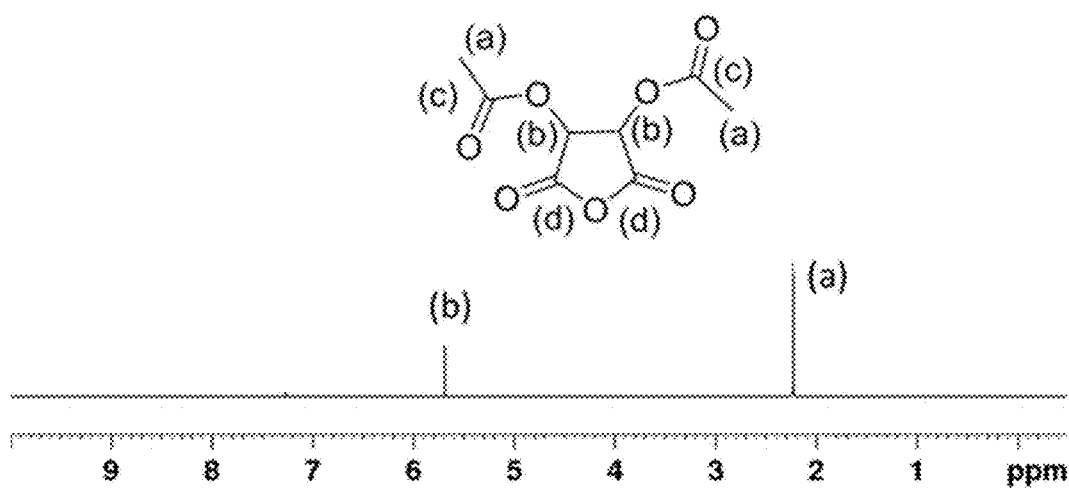
FIGS. 1A-1B are the $^1$H (FIG. 1A) and $^{13}$C (FIG. 1B) NMR spectra of diacetyl-L-tartaric anhydride.

Disclosed herein are ionic surfactants that may be in liquid form, chiral and may form micelles and reverse micelles. As described herein, an ionic liquid may be created by combining a tartaric acid long chain monoalkylester and a benzyl amine.

An ionic liquid may be formed by reacting the lauryl ester of diacetyl-L-tartaric acid, with a benzyl amine, such as (S)-(−)-α-methylbenzylamine. Tartaric acid is an unconventional and unprecedented starting material for the synthesis of ILs. The preparation of the chiral surface active anionic liquid (SAIL), T12M, is straightforward and can be designed to completely eliminate bi-products. Such ionic liquids may also be synthesized using enantiomers or diastereomers of the starting materials, ester or ether substitutions in place of acetyl groups in the tartaric acid moiety, variable length alkyl side chain, and/or counter ions which can be chiral or achiral organic or inorganic in nature.

T12M features an unprecedented combination of characteristics not previously found in other ionic liquids (ILs). T12M is the first surface active ionic liquid that is fully chiral, by virtue of the presence of chirality in both anionic head group and the counter-ion. T12M remains as a room temperature IL for 3 days and then transforms to a semi-solid with melting point at ~55° C. The d-spacings in solid and lyophilized aqueous T12M, are 13.89 Å and 14.54 Å respectively. T12M dissolves in both hydrogen bonding (water) and non-hydrogen bonding (chloroform) solvents and forms anionic chiral micellar aggregates (CMAs) and reverse-CMAs, at very low concentrations 0.32 mM and ~10 mM, respectively. CMAs of T12M adopt structures ranging from spherical to lamellar in shape in water in the 10-200 mM range; however, the zeta potential remains constant at ~−13 mV. The alkyl chains are interdigitated in the CMAs of T12M in water forming lamellar structures, yet are extended outwards forming reverse micelles in CHCl$_3$. With these characteristics, the chiral SAIL is able to function at all kinds of interfaces for various applications, and may be classified among the rarest detergent and/or stabilizing agents.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "alkyl," as used herein, means a straight or branched, saturated hydrocarbon chain. The term "C$_{1-4}$alkyl" means a straight or branched chain hydrocarbon containing from 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, 4,4-dimethylpentan-2-yl, n-heptyl, n-octyl, n-nonyl, and n-decyl.

The term "C$_{3-4}$cycloalkyl," as used herein, refers to a carbocyclic ring system containing three to four carbon atoms, zero heteroatoms and zero double bonds, i.e., cyclopropyl or cyclobutyl.

The term "carbocyclic ring," as used herein, refers to an all-carbon ring system that may be aromatic or non-aromatic. Representative example monocyclic carbocyclic rings include cyclopentane, cyclopentene, cyclohexane, cyclohexene, and benzene. A 5- to 7-membered carbocyclic ring may be fused to a phenyl to form, for example, an indane, indene, naphthalene, or tetrahydronaphthlene.

The term "halogen" or "halo," as used herein, means Cl, Br, I, or F.

The term "haloalkyl," as used herein, means an alkyl group, as defined herein, in which one, two, three, four, five, six, seven or eight hydrogen atoms are replaced by a halogen.

The term "4- to 7-membered heterocycle," as used herein, means a non-aromatic monocyclic ring having four, five, six, or seven ring atoms and containing at least one heteroatom independently selected from O, N, and S. Representative examples of 4- to 7-membered heterocycles include, but are not limited to, azetidine, azepane, diazepane, morpholine, piperazine, piperidine, pyrrolidine, tetrahydropyridine, and thiomorpholine.

The term "critical micelle concentration," as used herein, means the concentration above which micelles formed. Herein, this value was determined by measuring the concentration at which the slope of the decrease in surface tension meets equilibrium surface tension.

2. COMPOUNDS

In one aspect, compounds of the invention have formula (I), wherein $R^1$, $R^2$, $R^3$, $R^4$, $R^5$, $R^6$, $R^7$, n, and X— are as defined herein. The embodiments described herein include all combinations of $R^1$, $R^2$, $R^3$, $R^4$, $R^5$, $R^6$, $R^7$, n, and X—.
In some embodiments, $R^1$ is hydrogen.
In some embodiments, $R^2$ is hydrogen.
In some embodiments, $R^1$ and $R^2$ are hydrogen.
In some embodiments, $R^3$ is $C_{1-4}$alkyl. In some embodiments, $R^3$ is $CH_3$. In some embodiments, $R^1$ and $R^2$ are hydrogen and $R^3$ is $CH_3$.
In some embodiments, n is 0. In some embodiments, $R^3$ is $CH_3$. In some embodiments, $R^1$ and $R^2$ are hydrogen, $R^3$ is $CH_3$ and n is 0.
In some embodiments, $R^5$ is —C(O)$C_{1-4}$alkyl. In some embodiments, $R^5$ is —C(O)$CH_3$.
In some embodiments, $R^6$ is —C(O)$C_{1-4}$alkyl. In some embodiments, $R^6$ is —C(O)$CH_3$. In some embodiments, $R^5$ and $R^6$ are —C(O)$CH_3$.
In some embodiments, $R^7$ is $C_{10-14}$alkyl. In some embodiments, $R^7$ is $C_{12}$alkyl. In some embodiments, $R^7$ is straight chain $C_{12}$alkyl. In some embodiments, $R^5$ and $R^6$ are —C(O)$CH_3$ and $R^1$ is $C_{12}$alkyl. In some embodiments, $R^5$ and $R^6$ are —C(O)$CH_3$ and $R^7$ is straight chain $C_{12}$alkyl.
In some embodiments, the compound of formula (I) has formula (I-a)

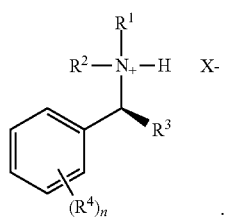

(I-a)

In some embodiments, the compound of formula (I) has formula (I-b)

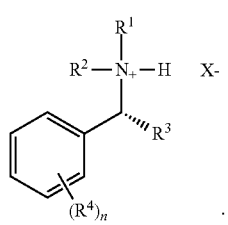

(I-b)

In some embodiments, formula (II) is formula (II-a)

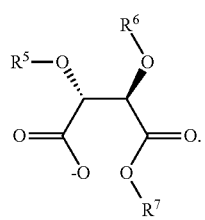

(II-a)

The compound may exist as a stereoisomer wherein asymmetric or chiral centers are present. The stereoisomer is "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The disclosure contemplates various stereoisomers and mixtures thereof and these are specifically included within the scope of this invention. Stereoisomers include enantiomers and diastereomers, and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry," 5th edition (1989), Longman Scientific & Technical, Essex CM20 2JE, England, or (2) direct separation of the mixture of optical enantiomers on chiral chromatographic columns, or (3) fractional recrystallization methods.

It should be understood that the compound may possess tautomeric forms, as well as geometric isomers, and that these also constitute embodiments of the disclosure.

The present disclosure also includes an isotopically-labeled compound, which is identical to those recited in formula (I), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Substitution with heavier isotopes such as deuterium, i.e. $^2H$, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) are $^{11}C$, $^{13}N$, $^{15}O$, and $^{18}F$. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

3. COMPOSITIONS AND FORMULATIONS

In one aspect, disclosed are ionic liquids comprising a plurality of the compounds disclosed herein. The ionic liquid may be surface active. In some embodiments, the ionic liquid may be chiral.

In another aspect, disclosed are compositions comprising the compounds disclosed herein.

In some embodiments, the compositions further comprise an aqueous medium. In some embodiments, the compositions further comprise an aqueous medium, wherein the compound has a critical micelle concentration of about 0.0001-0.0005 M in the aqueous medium. The compound may have a cirical micelle concentration of about 0.0001-0.0004 M, about 0.0001-0.0003 M, about 0.0002-0.0005 M, about 0.0003-0.0005 M, about 0.0004-0.0005 M, about 0.0002-0.0004 M, or about 0.0003-0.0004 M in the aqueous medium.

In some embodiments, the compositions further comprise a micellar aggregate, the micellar aggregate comprising a plurality of compounds disclosed herein. Micellar aggregates may contain a varying number of compounds in the aggregate. The aggregation numbers may be greater than 50, greater than 100, greater than 150, greater than 200, or greater than 250. The aggregation numbers may be concentration dependent.

The micellar aggregate may form various micelle shapes. In some embodiments, the micellar aggregate comprises a spherical micelle, a rod-like micelle, and/or a lamellar structure. The shape of the micellar aggregate may be concentration dependent.

In some embodiments, the compositions further comprise an organic medium, i.e., a non-aqueous solvent such as a non-polar aprotic organic solvent (e.g., a halogenated solvent such as chloroform). In some embodiments, the compositions further comprise an organic medium, wherein the compound has a critical micelle concentration of about 0.003-0.1 M in the organic medium. The compound may have a cirical micelle concentration of about 0.003-0.075 M, about 0.003-0.05 M, about 0.003-0.04 M, about 0.003-0.02 M, about 0.005-0.1 M, about 0.005-0.05 M, about 0.005-0.03 M, about 0.01-0.1 M, about 0.01-0.05 M, about 0.01-0.03 M, about 0.03-0.1 M, about 0.03-0.05 M, or about 0.05-0.1 M in the organic medium.

In some embodiments, the compositions further comprise a reverse micellar aggregate, the reverse micellar aggregate comprising a plurality of compounds disclosed herein.

4. EXAMPLES

Abbreviations used in the descriptions of following examples: T12M is dodecyl ester of diacetyltartaric acid; SAIL is surface active ionic liquid; CMA is chiral micellar aggregate; CMC is critical micelle concentration; CIL is chiral ionic liquid; T12OH is lauryl monoester of diacetyl-L-tartaric acid; MBA is (S)-(−)-α-methylbenzylamine; NMR is nuclear magnetic resonance spectroscopy; 2D-ROSEY is two-dimensional nuclear magnetic resonance spectroscopy, VCD is vibrational circular dichroism; VA is vibrational absorption; ECD is electronic circular dichroism; EA is electronic absorption; SSFQ is steady-state fluorescence quenching; CPC is cetylpyridinium chloride; DMBP is 3,4-dimethylbenzophenone; DLS is dynamic light scattering measurements; DSC is differential scanning calorimetry; and L-DTA is diacetyl-L-tartaric anhydride.

Example 1. Synthesis of Diacetyl-L-Tartaric Anhydride (L-DTA), Lauryl Monoester of Diacetyl-L-Tartaric Acid (T12OH) and Chiral Anionic Liquid (T12M)

Scheme 1 shows an exemplary synthesis of T12OH.

Scheme 1:

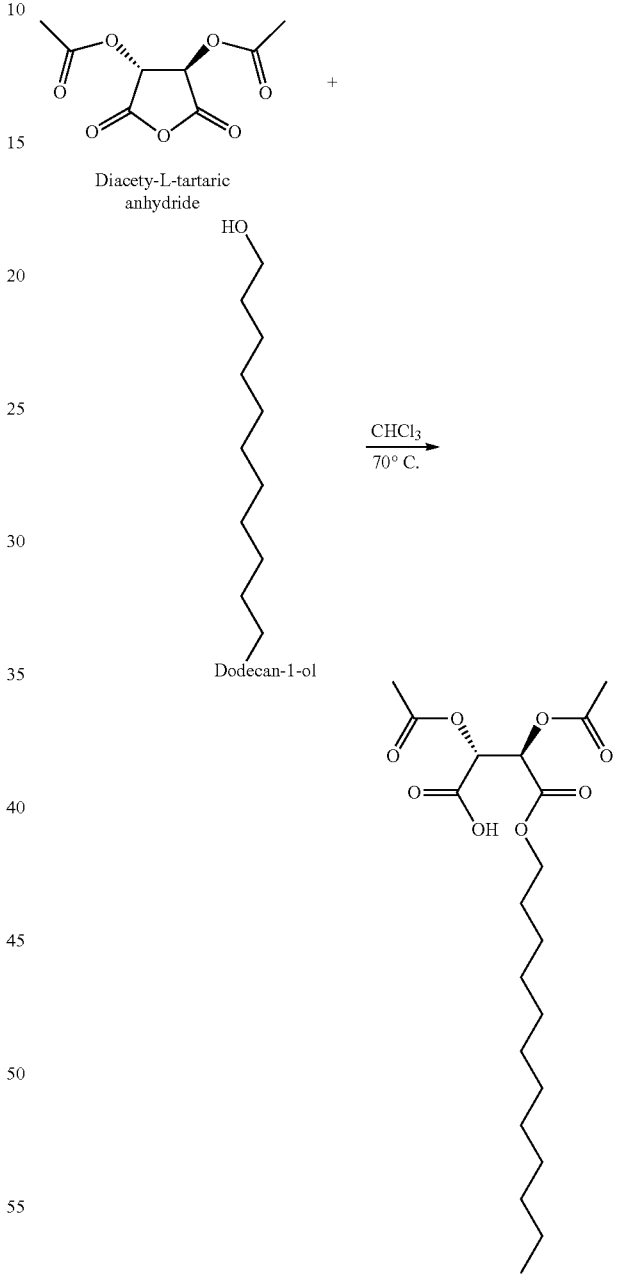

Diacetyl-L-Tartaric Anhydride (L-DTA).

L-DTA was first synthesized to prepare the lauryl monoester of diacetyl-L-tartaric acid. The synthesis of L-DTA was accomplished by a reaction between 10 g (0.028 mole) of L-tartaric acid and 15.8 mL of acetic anhydride (0.167 mole) containing 0.15 mL of concentrated sulfuric acid under reflux conditions for 15 minutes. The crude product was cooled in an ice bath and was collected on a Buchner funnel. The product was washed with benzene twice and then with diethyl ether. The product was dried under vacuum.

Lauryl Monoester of Diacetyl-L-Tartaric Acid (T12OH).

1.6 mL of dodecanol (6.9 mmole) and 3 g of L-DTA (13.9 mmole) were reacted under inert atmosphere in chloroform under reflux conditions. L-DTA was added in small increments of 0.5 g. The reaction was allowed to stir overnight. The crude product was collected and washed with 0.1 M hydrochloric acid several times by repeated use of vortex shaker and centrifugation. Finally, chloroform was added and the organic layer was extracted. The $CHCl_3$ was evaporated under vacuum. Diethyl ether was added to dissolve the product, and the solution was dried over $MgSO_4$. The product was obtained by evaporating diethyl ether under vacuum.

Chiral Anionic Liquid (T12M).

T12OH was mixed with 1 equivalent of (S)-(−)-α-methylbenzylamine (MBA), to obtain the chiral ionic liquid, T12O−MBA+, designated as T12M.

Example 2. Spectral Characterization and Properties $^1$H, $^{13}$C NMR and 2D ROESY Experiments:

$^1$H, $^{13}$C NMR and 2D-ROSEY experiments were performed using a Bruker 400 MHz spectrometer equipped with a 9.4 Tesla Oxford magnet, which is controlled by a Bruker AV-400 console.

Differential Scanning Calorimetry:

Differential scanning calorimeter (DSC) experiments were run at 10° C./min under nitrogen on a TA Instruments Q1000.

Vibrational and Electronic Circular Dichroism:

Vibrational circular dichroism (VCD) and associated vibrational absorption (VA) measurements were made using ChiralIR spectrometer. A 50 μm fixed path length cell, with $BaF_2$ windows was used. Electronic circular dichroism (ECD) and associated electronic absorption (EA) measurements were made using a JASCO 720 spectrometer using a 0.01-1 cm quartz cells.

X-Ray Diffraction Measurements:

The X-ray diffraction patterns of T12M were measured by Scintag X-1 powder X-ray diffractometer using a zero background sample holder and a monochromatic Cu Ka (45 kv, 40.8 mA) radiation (1.54 A°) in 2θ ranges of 1 to 25°.

Figure 1B:
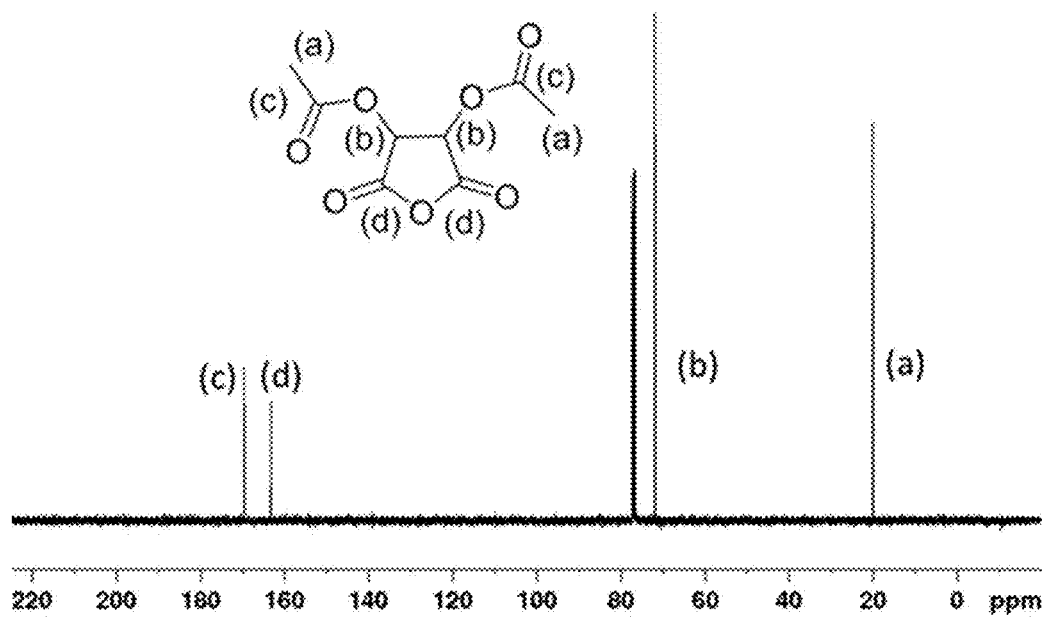
Figure 2A:
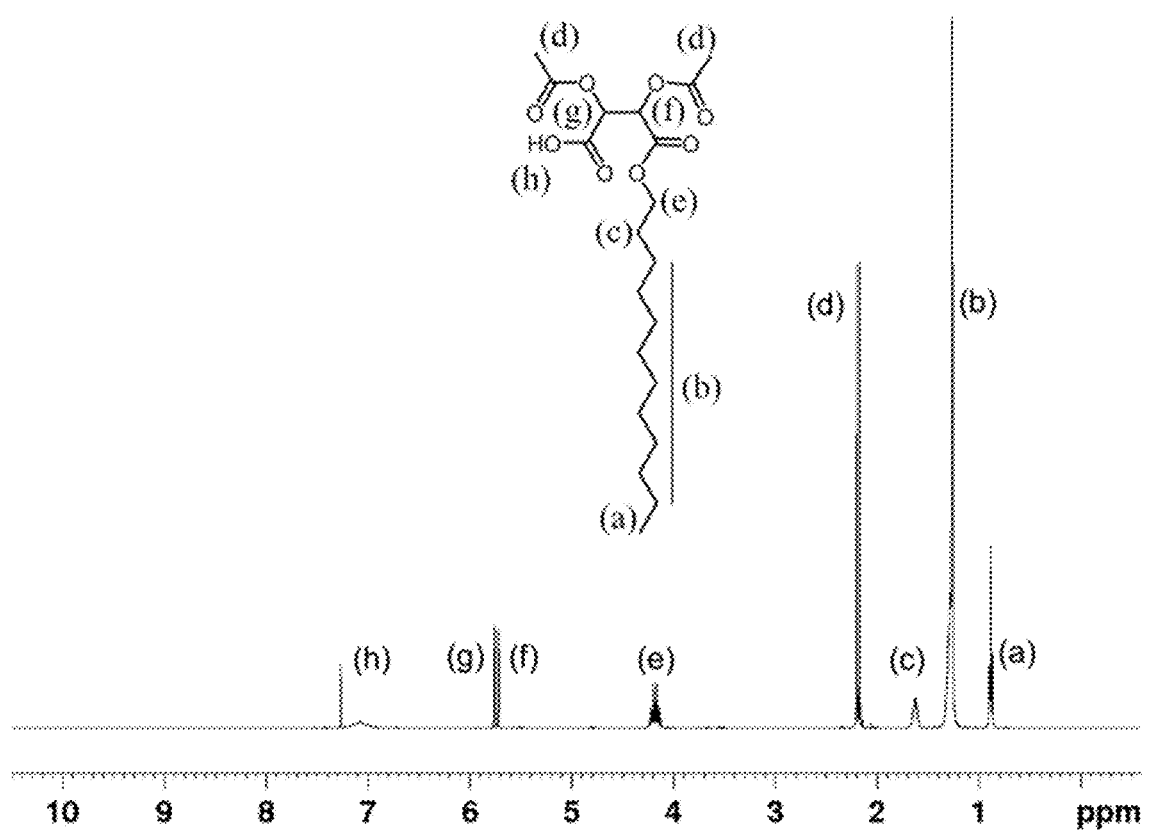
FIGS. 2A-2B are the $^1$H (FIG. 2A) and $^{13}$C (FIG. 2B) NMR spectra of the lauryl monoester of diacetyl-L-tartaric anhydride (T12OH).
Figure 2B:
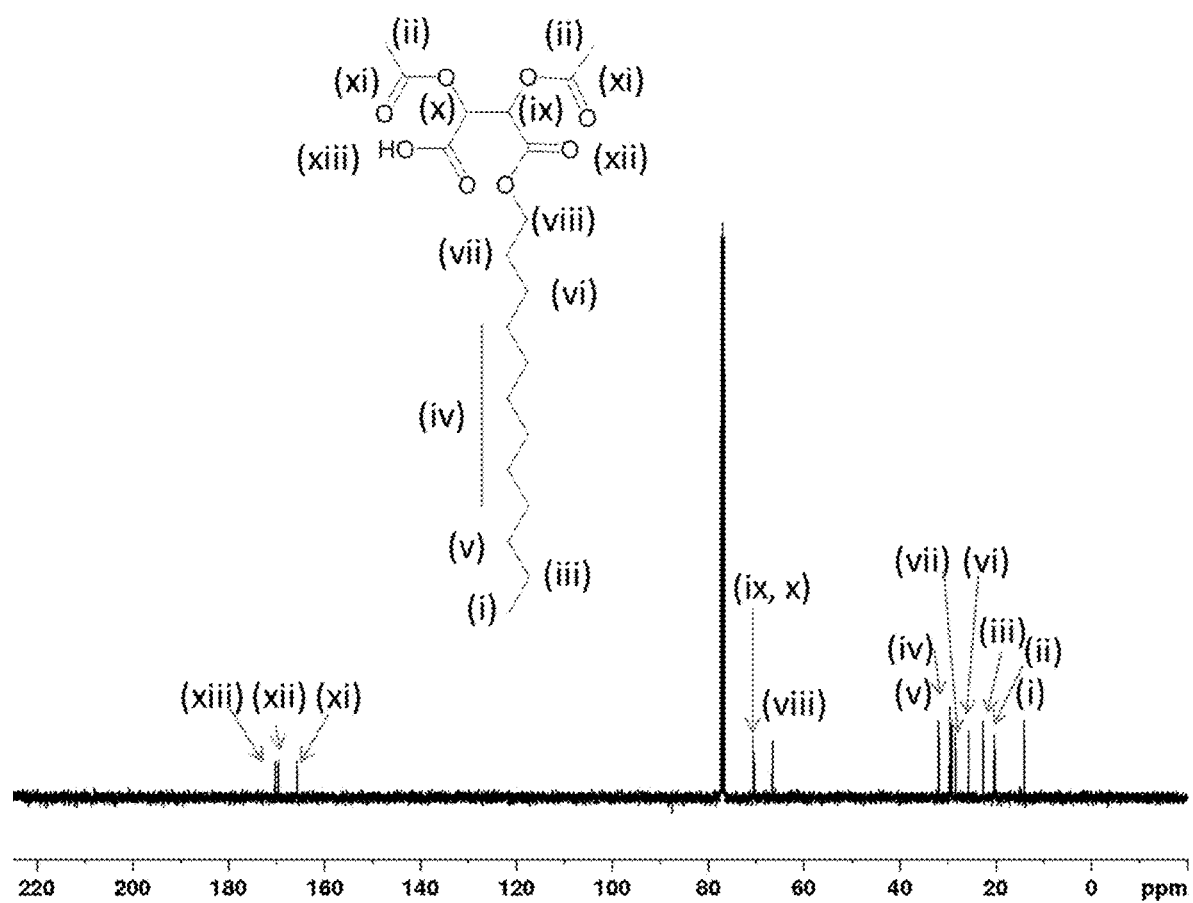

The $^1$H and $^{13}$C NMR spectra of L-DTA and T12OH are presented in FIG. 1 and FIG. 2. The purity of L-DTA was estimated from the integral value at δ:2.2 and 5.7 ppm, corresponding to protons of acetyl group and methine group, and was found to be >99%. For T12OH, the purity was >98% and was assessed from the integral value at δ:0.8 and 5.5 ppm, corresponding to methyl group (alkyl chain) and methine group.

In order to take the reaction between anhydride and dodecanol to completion, 2:1 mole equivalents of anhydride: dodecanol were used, as it was difficult to remove dodecanol from the crude product. However, the use of reactants at 1:1 mole ratio and without solvents yielded the product with purity >97% and without any bi-products. The purity of T12OH was reproducible only when freshly synthesized L-DTA was used, instead of the commercially available L-DTA. The commercially available L-DTA degraded with time on storing and led to issues with reproducibility. The purity of T12OH could not be increased any further by simple washings. T12OH foams in water, so sparingly soluble T12OH and its highly soluble sodium salt, T12O$^−$ Na$^+$, may be used as chiral surfactants. Attempts to remove diacetyl-L-tartaric acid from T12OH using water did not work due to the formation of an emulsion, which could not be broken with addition of NaCl solution. However, the use of 0.1 M HCl solution for washing selectively decreased the solubility of T12OH in water, which facilitated the removal of diacetyl-L-tartaric acid impurities. The emulsion formed by T12OH in 0.1 M HCl could be easily broken by centrifugation.

T12OH is a liquid at room temperature (~24+1° C.), even though diacetyl-L-tartaric acid and dodecanol exist as a solid and paste respectively. This observation indicated that diacetyl tartaric acid when attached to a long chain alcohol of suitable length can destabilize the solid-phase crystals, similar to the properties of imidazolium ions. T12M, obtained by mixing T12OH with liquid (S)-MBA, also existed as a liquid for 3 days. The use of any non-toxic and biodegradable liquid counter ion, in lieu of MBA used here for proof-of-principle, would be expected to make the resulting SAIL completely non-toxic and biodegradable.

Figure 3:
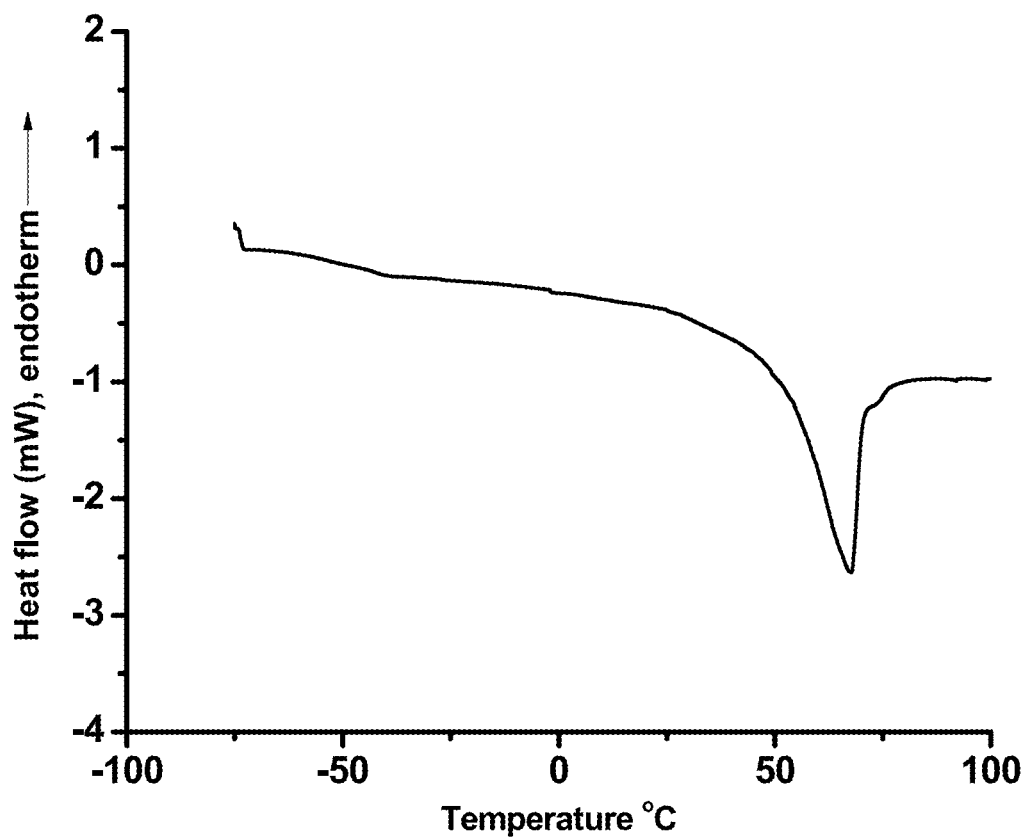
FIG. 3 shows the DSC trace of chiral anionic liquid (T12M) on day 5.

T12M existed as a liquid at room temperature for 3 days, became pasty on the fourth day and finally appeared as wet solid on 5th day. The differential scanning calorimetry (DSC) trace of T12M after equilibration for 5 days (FIG. 3) showed only one endotherm with an onset temperature at 51° C., which was verified with melting point analysis of solid T12M. The absence of other endotherms indicated that T12M existed in one phase on day 5. The existence of T12M as a room temperature ionic liquid (IL) for 3 days was uncommon. Nevertheless, T12M may offer both the benefits of a room temperature and a high temperature IL.

High temperature SAILS can be hugely beneficial for emulsion polymerization techniques. Emulsion polymerization is usually performed at 60-70° C. At this temperature T12M can act as solvent or surfactant. After polymerization, excess T12M could be recovered by simply storing the emulsion at room temperature as described for conventional surfactants.

The structure of T12M solid, after 5 days of equilibration, was investigated using low angle powder X-ray diffraction data, as governed by Bragg's law (Equation 1):

$$n\lambda = 2d_{hkl} \sin \theta_{hkl} \quad (1)$$

where n is an integer; λ is the wavelength of probe radiation; d is the spacing between diffraction planes defined by Miller indices h, k, and l; and θ is the diffraction angle. The d-spacings of successive peaks of lamellar and hexagonal structures appear in the ratio (1:0.5:0.33) and (1:0.71:0.58) respectively.

Figure 4:
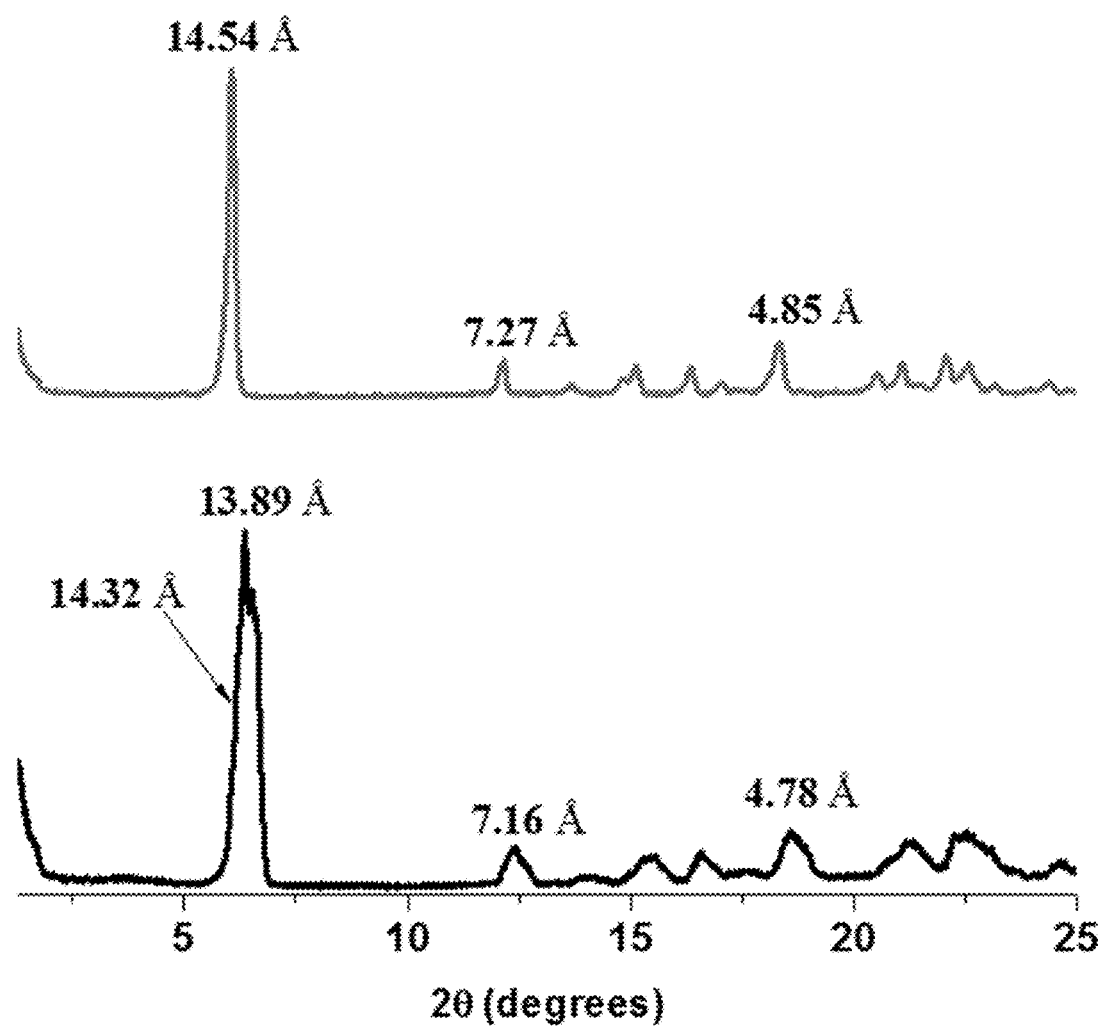
FIG. 4 shows the powder X-ray diffraction data of T12M lyophilized from a 200 mM aqueous solution (top) and solid (bottom).

The powder X-ray diffraction data of T12M solid, with T12M lyophilized from 200 mM aqueous solution, are shown in FIG. 4. The T12M lyophilized from a 200 mM aqueous solution showed peak positions in the ratio 1:0.5: 0.33 which indicated the presence of lamellar structure. The corresponding ratios for T12M solid, 1:0.52:0.34, indicated slightly distorted lamellar structures. The d-spacings for T12M lyophilized from water (200 mM) and for solid, respectively, were at 14.54 Å and 13.89 Å, and were less than the length of a hydrophobic chain, 16.68 Å, derived from Tanford equation (Equation 2):

$$L_{max} = 1.5 + 1.265n \quad (2)$$

where $L_{max}$ is maximum stretching length of alkyl chain and n is number of carbons in the alkyl chain. This observation indicated that alkyl chains were interdigited in both (i.e. T12M after 5 days of equilibration and T12M lyophilised from 200 mM aqeous solution). T12M liquid upon dissolution in water at 200 mM, and lyophilization, acquired a well-organized lamellar structure which was evident from the X-ray difraction data of the lyophilized sample. On the other hand, the slow transformation of T12M liquid, upon equilibration, to solid involved the transformation of a disorganized liquid structure to a partially organized lamellar structure. A single chain surfactant, with a relatively short chain, forming lamellar structure is rare. Also, high molecular weight room temperature SAILs are rare. It is unclear if the high molecular weight room temperature SAILs previously reported remain as liquid for prolonged periods or transform to pasty substances with time similarly to T12M, because SAILS are known to have the propensity to aggregate.

Figure 5A:
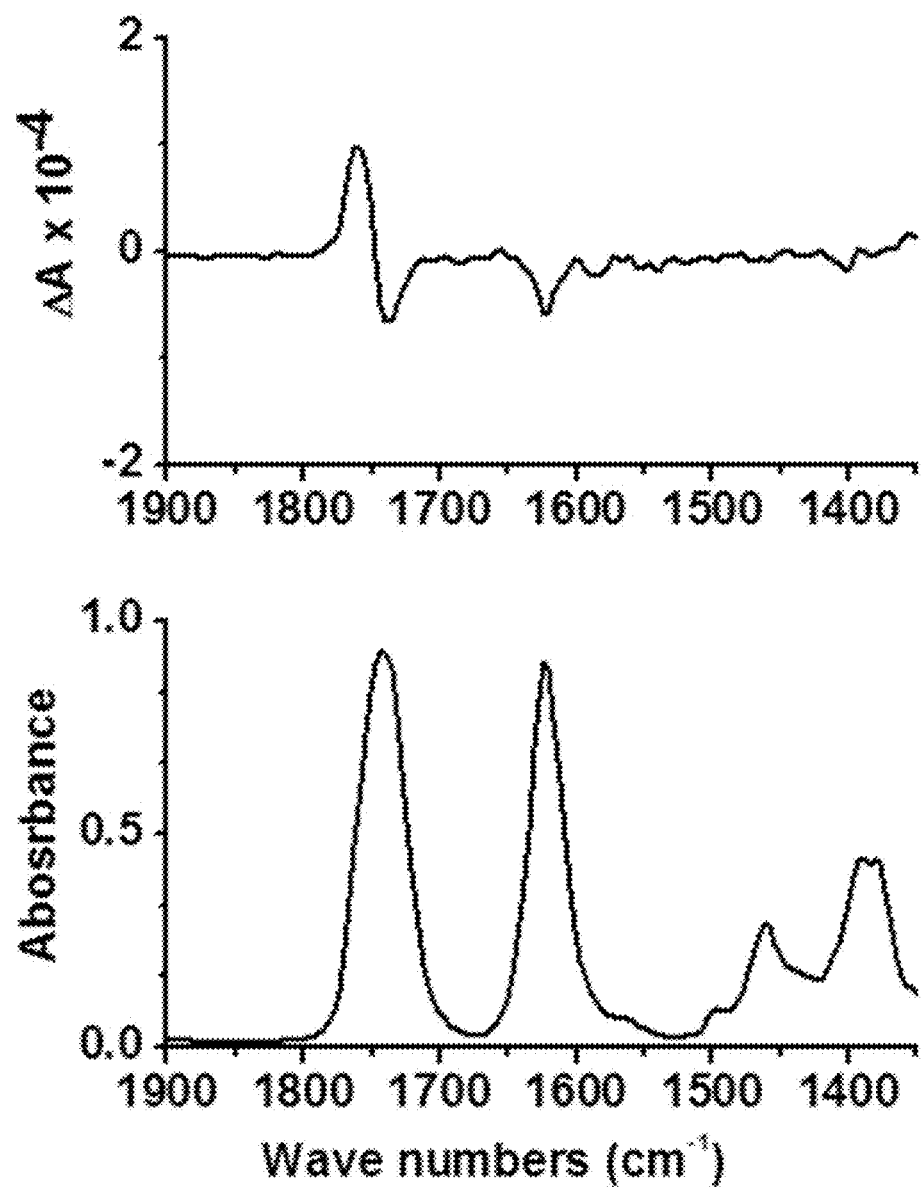
FIGS. 5A-5B are circular dichroism spectra of T12M.
Figure 5B:
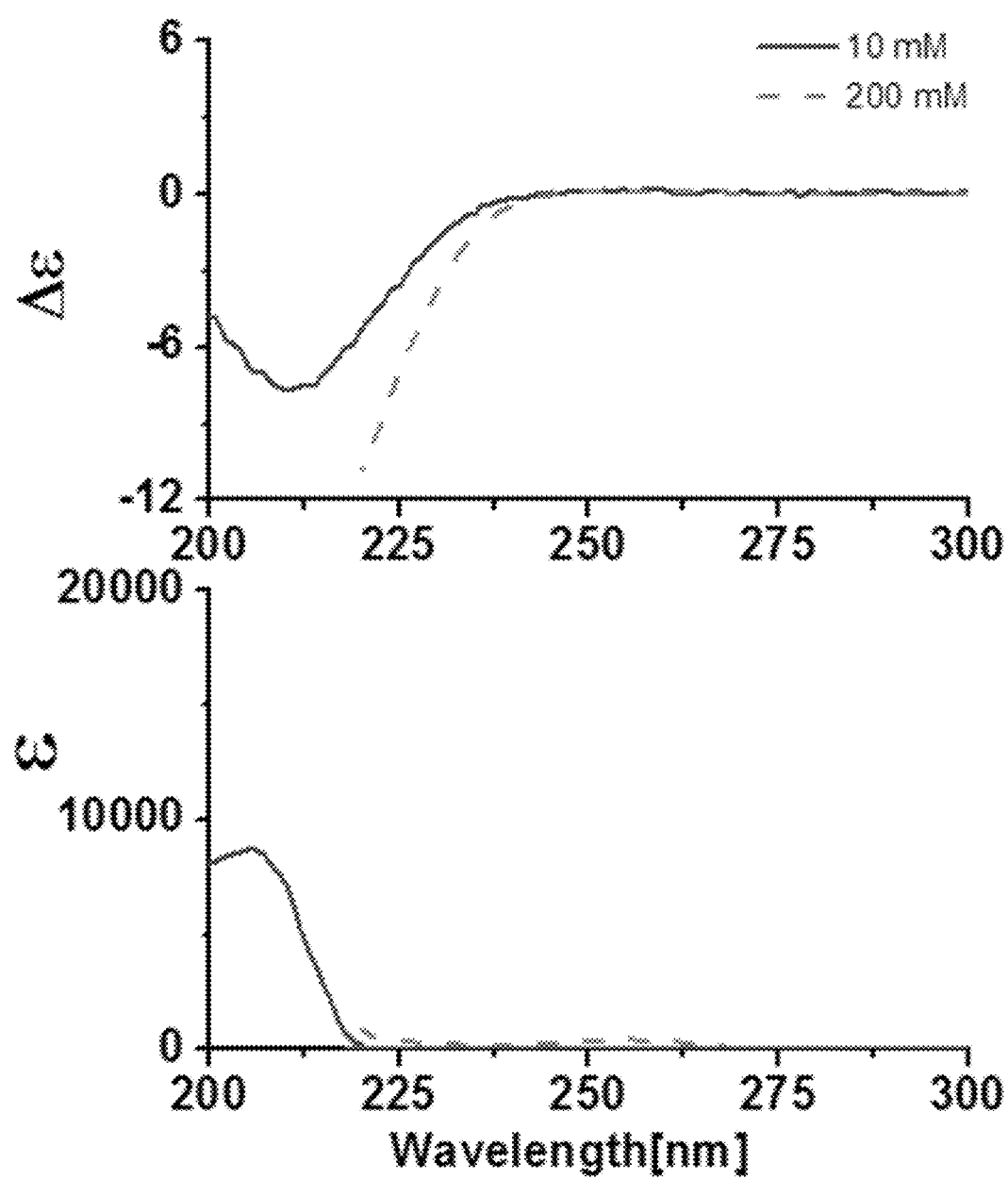

The chiroptical properties of T12M were characterized using VCD/VA and ECD/EA as shown in FIG. 5. In the vibrational spectra of a 200 mM aqueous T12M solution, the band at 1743 cm$^{-1}$ was associated with the ester carbonyl group; the band at 1623 cm$^{-1}$ was associated with COO$^{-}$ group; the bands at 1562 cm$^{-1}$, 1500 and 1458 cm$^{-1}$ were associated with C=C stretching vibrations of the MBA; and the band at 1384 cm$^{-1}$ was associated with CH bending vibrations. The VCD spectrum showed a bisignate couplet corresponding to the carbonyl group stretching vibrations at 1743 cm$^{-1}$ and a negative VCD associated with stretching vibration of COO— group. The electronic spectra of aqueous T12M solutions at 10 and 200 mM spectrum showed an absorbance peak at ~212 cm$^{-1}$ associated with negative ECD.

Example 3. Surface Properties, Micellization Parameters and Aggregation Behavior Tensiometry:

Surface tension measurements were performed on a Fisher Scientific tensiometer (Model 21), employing a platinum du Nuoy ring as the probe. The surface tension values reported here are the averages of at least three measurements and represent the equilibrium values.

Steady-State Fluorescence Quenching (SSFQ) Experiments:

SSFQ experiments were performed to determine the aggregation number of T12M in water and to estimate the CMC of T12M in CHCl$_3$.

Estimation of Aggregation Numbers:

Pyrene was used as the fluorescence probe. Cetylpyridinium chloride (CPC) quencher was used for T12M concentrations at 10 and 50 mM. 3,4-dimethylbenzophenone (DMBP) was used as quencher for T12M concentrations at 100 and 200 mM. In view of low solubility of pyrene in water (1×10$^{-7}$ M), a required volume of stock solution of pyrene in methanol (1×10$^{-4}$ M) was pipetted into a standard flask, and a thin film of pyrene was deposited on the side of the flask through evaporation of solvent and purging with N$_2$ gas. The effective concentration of pyrene was maintained at 1×10$^{-6}$ M in all of the solutions. The concentration of the quencher was varied from 9×10$^{-5}$ M to 12×10$^{-4}$. The fluorescence spectra of pyrene in T12M solutions and in the presence of quencher at different concentrations were recorded with a JASCO spectrofluorometer FP-8300. The slit widths of excitation and emission were maintained at 5 nm. The excitation wavelength (λexc) was set at 337 nm and that of emission was set at 374 nm. The aggregation numbers, N, of T12M were determined using the Equations 3 and 4.

$$\left(\frac{I_o}{I_q}\right) = \exp\left(\frac{[q]}{[\text{micelle}]}\right) \quad (3)$$

$$N = \exp\left(\frac{[c - CMC]}{[\text{micelle}]}\right) \quad (4)$$

where $I_o$ and $I_q$ are the intensities of fluorescence emission at 374 nm of pyrene in the absence and presence of the quencher of concentration [q], respectively. c is the total surfactant concentration. All measurements were performed at 24±0.1° C.

Estimation of CMC of T12M in CHCl3:

T12M solutions in CHCl$_3$ in the 1×10$^{-3}$-200 mM range were added to flasks containing pyrene. The effective concentration of pyrene was maintained at 1×10$^{-6}$ M. The pyrene was deposited in the same manner as it was deposited to estimate aggregation number. The ratio of the intensities of the third I$_3$ (384 nm) to first I$_1$ (373 nm) vibronic peak of the fluorescence spectrum of the pyrene probe was used as an estimate of the micropolarity of the pyrene microenvironment.

Dynamic Light Scattering Measurements (DLS):

DLS measurements were carried out to get an estimate of the size of aggregated structures and to estimate the CMC for T12M solutions. The measurements were performed using a DLS Malvern Nano ZS. The samples were filtered using 0.45 μm membrane filter.

Figure 6:
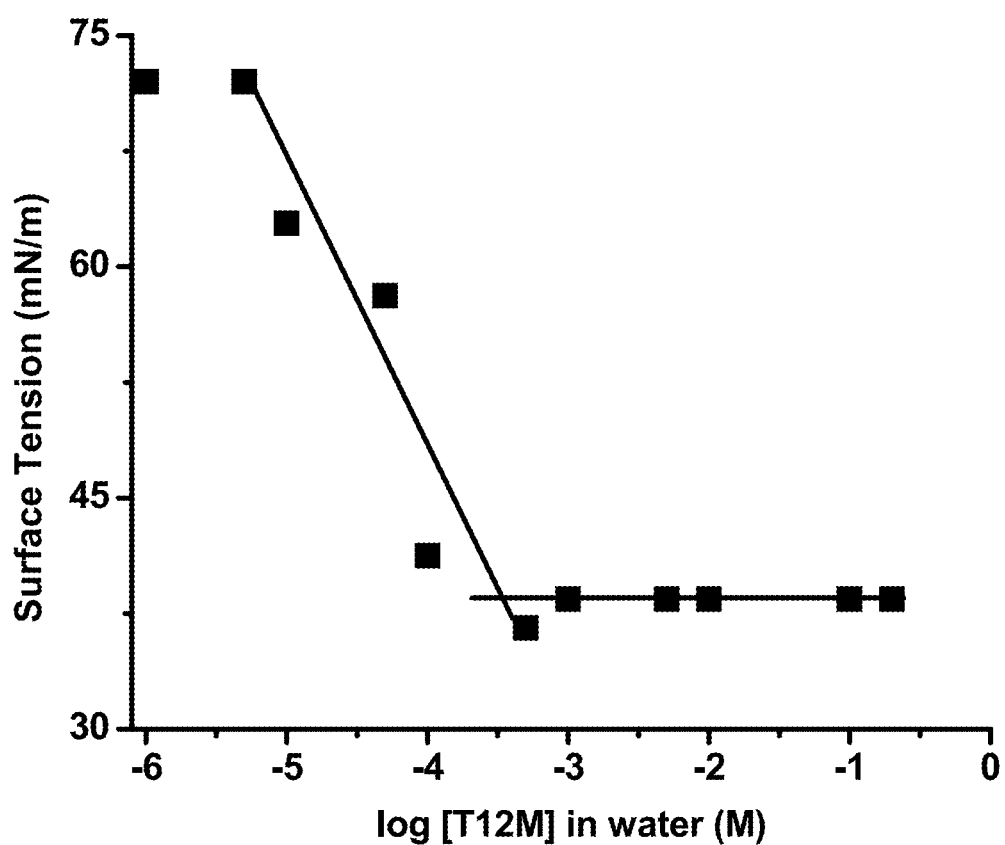
FIG. 6 is the surface tension profile of T12M.

The plot of surface tension (γ) versus molar concentration of T12M on the log scale (log C) is shown in FIG. 6. γ very steeply decreased from about 72 mN/m to about 36 mN/m over the narrow concentration range of 1×10$^{-5}$ to 3.2×10$^{-4}$ M (FIG. 6). Above the concentration of 3.2×10$^{-4}$ M, γ remained almost constant at 38 mN/m, indicative of coverage of the air/solution interface with a monolayer of T12M. The concentration corresponding to the onset of γ$_c$, 3.2×10$^{-4}$ M, was taken as the critical micelle concentration (CMC); the concentration at which the slope of the decrease in surface tension meets equilibrium surface tension. The value of pC$_{20}$, which measures the efficiency of adsorption of the surfactant at the air-water interface, was high at 4.2. The low CMC of T12M in comparison to those for conventional surfactants was due to the mutifunctionality in the head group. Several SAILs and cationic/anionic surfactants with multifunctionality in the head group were endowed with low CMC and better interfacial characteristics. It was previously reported that COOH-functionalized imidazolium-based SAILs possess lower CMC and superior surface activity compared to homologous non-functionalized SAILs. Long-chain β-hydroxy-γ-alkyloxy-N-methylimidazolium ILs have superior surface activity compared with the simple alkyl-substituted derivatives. Several cationic/anionic surfactants have been previously synthesized with mutifunctionality in the head group which conferred low CMC and better interfacial characteristics to the surfactant.

A cationic surfactant from tyrosine, with mutifunctionality in the head group, had physiochemical properties similar to nonionic surfactants and with low CMC at ~10$^{-5}$M.

Applying the Gibbs adsorption isotherm equation (Equation 5), the surface coverage (Γ) and minimum surface area (α) of packing/molecule were estimated (Table 1).

$$\gamma = -nRT \ln C = -2.303nRT \log C, \ a = 10^{23}/N\Gamma \quad (5)$$

where γ refers to surface tension in mN/m, R refers to gas constant=8.31 J mol$^{-1}$ K$^{-1}$, T refers to temperature=298.15 K, Γ refers to surface excess concentration, C refers to concentration in mol/L, a refers to area per molecule at the interface in Å$^2$ and n=(1+α), where α is the fractional dissociation. For 1:1 ionic surfactants, α=1 and n=2. In the presence of swamping electrolyte containing common non surfactant ion, n=1. As α for T12M was not assessed, the packing characteristics of T12M are summarized in Table 1 for both cases of n=1 and 2.

TABLE 1

Adsorption characteristics of T12M

| n | Γ (μmol/m$^2$) | a (Å$^2$/molecule) |
|---|---|---|
| 1 | 3.1 | 53 |
| 2 | 1.6 | 106 |

Figure 7A:
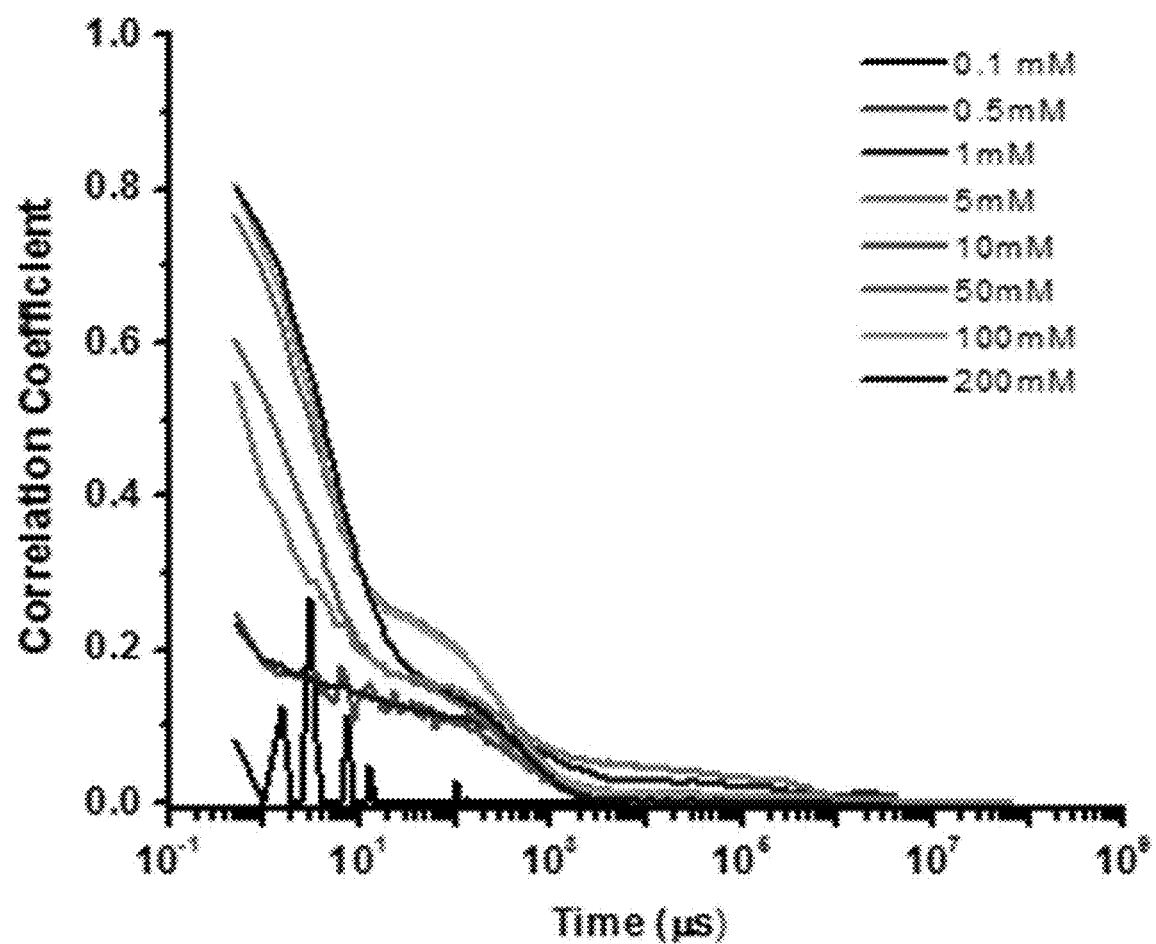
FIGS. 7A-7B are plots of the correlogram or correlation coefficient vs time (FIG. 7A) and photon counts (FIG. 7B) as a function of T12M concentration in water as determined by dynamic light scattering (DLS).
Figure 7B:
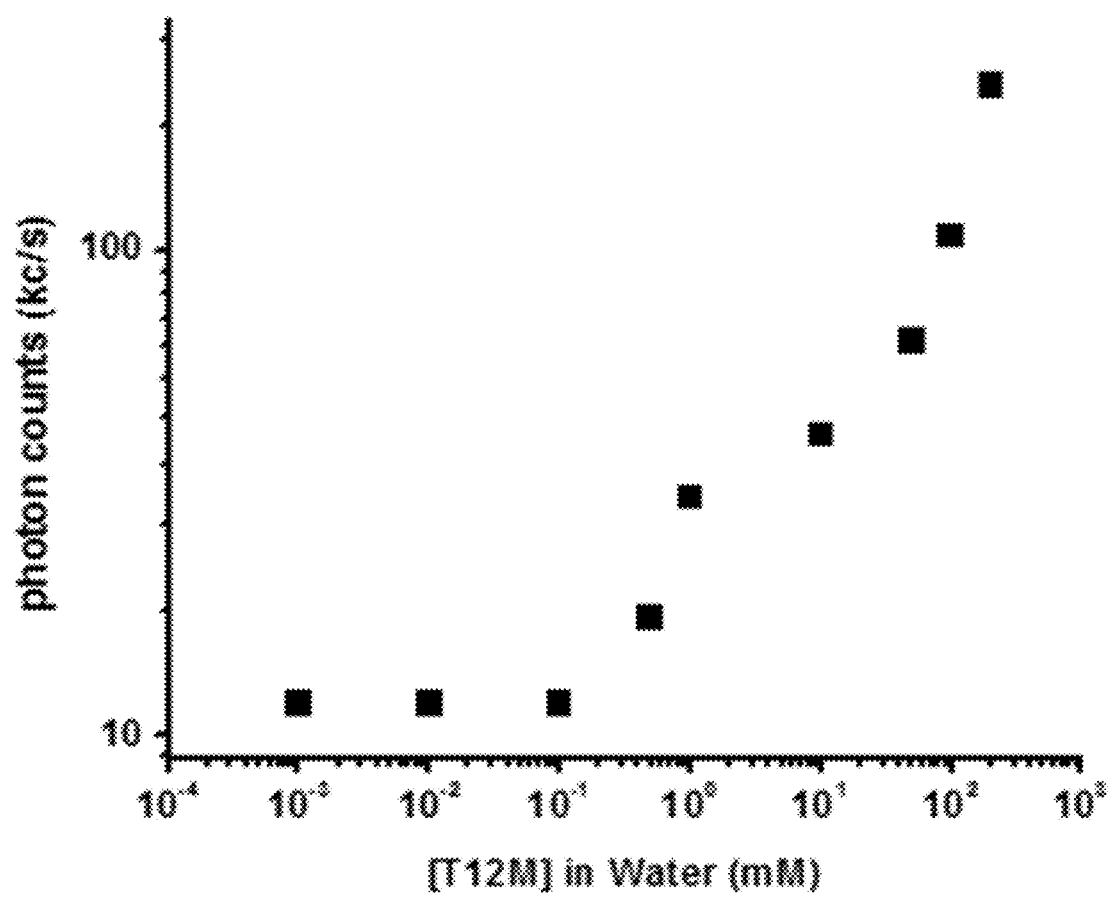

The CMC derived from tensiometry was corroborated with correlation coefficient vs time at different concentrations, and photon counts vs concentrations, using DLS (FIG. 7). The plot of correlation coefficient vs. time is highly important but often ignored data that can be obtained from DLS, and, due to its extreme sensitivity, can be used to identify the presence of contaminants and in the estimation of size of the particles. The plot of correlation coefficient vs. time for T12M at 0.1 mM-200 mM is shown in FIG. 7A. The photon counts from back scattered light by T12M solution remained constant (FIG. 7B) at ~11.6 kc/s at concentrations 0.001-0.1 mM. At concentrations >0.1 mM, the intensity of the scattered light increased due to the presence of well-defined particles in the T12M solution. As a result the correlation coefficient increased with increases in concentration. The correlogram for T12M at 0.1 mM was not well defined, indicating the absence of aggregates at 0.1 mM. A well-defined correlogram for T12M was seen at 0.5 mM, indicating the formation of micelles at this concentration. The correlograms also showed the presence of a slow mode, as revealed by a small hump at ~10$^2$ μs, which may be due to unavoidable contaminants such dust particles, micro foam bubbles, viruses or even bacteria. The data from photon counts of laser light scattered by T12M solution (FIG. 7B) suggested that micelles begin to form at concentration >0.1 mM and the size of micelles increases with the surfactant concentration. The CMC deduced from the correlograms and photon counts in FIG. 7 was in close agreement with that from tensiometry.

Figure 8:
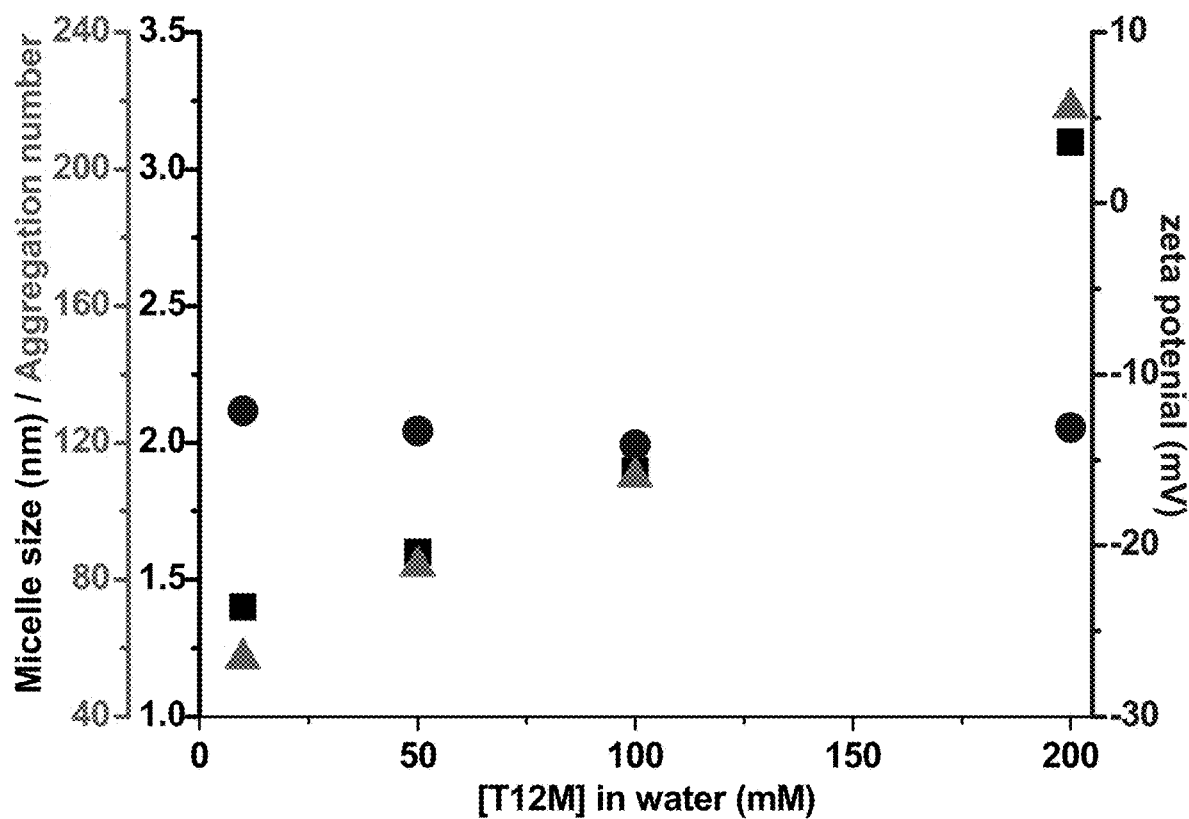
FIG. 8 shows micelle size (black, squares) and zeta potential (blue, circles) as determined by DLS, and aggregation number (pink, triangles) as determined by steady-state fluorescence quenching (SSFQ), for T12M at various concentrations in water.

The DLS data suggested that the mean micelle size of T12M, increased from 1.4-3.1 nm in the concentration range of 10-200 mM (FIG. 8). If this data was accurate, it would have indicated that the aggregation number (N) for T12M in the 10-200 mM range, determined from total surface area of the micelle (estimated from the size of micelles from DLS at respective concentrations) and the surface area per molecule estimated from tensiometry, was in the range of 4-6. Since N cannot be so small, it was inferred that the size of the micelles was underestimated by DLS. The underestimated size of micelles was likely due the interference caused by the scattering of light by the large, unavoidable particulate contaminants, the presence of which was confirmed by the presence of a small hump in the correlogram presented in FIG. 7A. Contaminants can interfere with the scattering of light by micelles because the micelles (a) do not have high refractive index and (b) are very small in comparison to contaminants. As per the Rayleigh approximation, the intensity of the scattered light is proportional to 6$^{th}$ power of its diameter. As a result, light from the larger contaminants can overwhelm the light scattered by smaller particles making it difficult to estimate the size of the smaller particles with sufficient accuracy.

Although the size of the aggregates determined by DLS appeared to be under-estimated, the trend in the growth of aggregates was real, as the increase in size of aggregates coincided with the aggregation numbers determined using SSFQ technique (FIG. 8). The aggregation numbers of T12M were determined to be 57, 84, 110 and 218 for concentrations at 10, 50, 100 and 200 mM, respectively. These aggregation numbers may be useful in accessing the shape of the aggregates. For instance, the aggregation number ~90 has been previously attributed to rod like micelle and <90 has been previously attributed to spherical micelles. Lamellar structures are known to have large aggregation number ~200. Therefore, the aggregation numbers of T12M in water determined from SSFQ demonstrated that CMAs of T12M exist as spherical micelles at 10 mM and as rod like micelles at 50 mM and in lamellar structures at 200 mM. The existence of T12M in lamellar structures at 200 mM corroborate the X-ray diffraction data of the lyophilized T12M solution at 200 mM. The zeta potential of T12M at 10-200 mM was almost constant at −13.8+0.8 mV (FIG. 8). Importantly, zeta potential data demonstrated that the aggregates were anionic in nature. In other words, all the MBAs do not form intimate ion pair with T12OH. Also, a constant zeta potential with increase in the size of micelles indicated that the ratio of T12OH:MBA was constant with the increase in the size of micelles.

Figure 9:
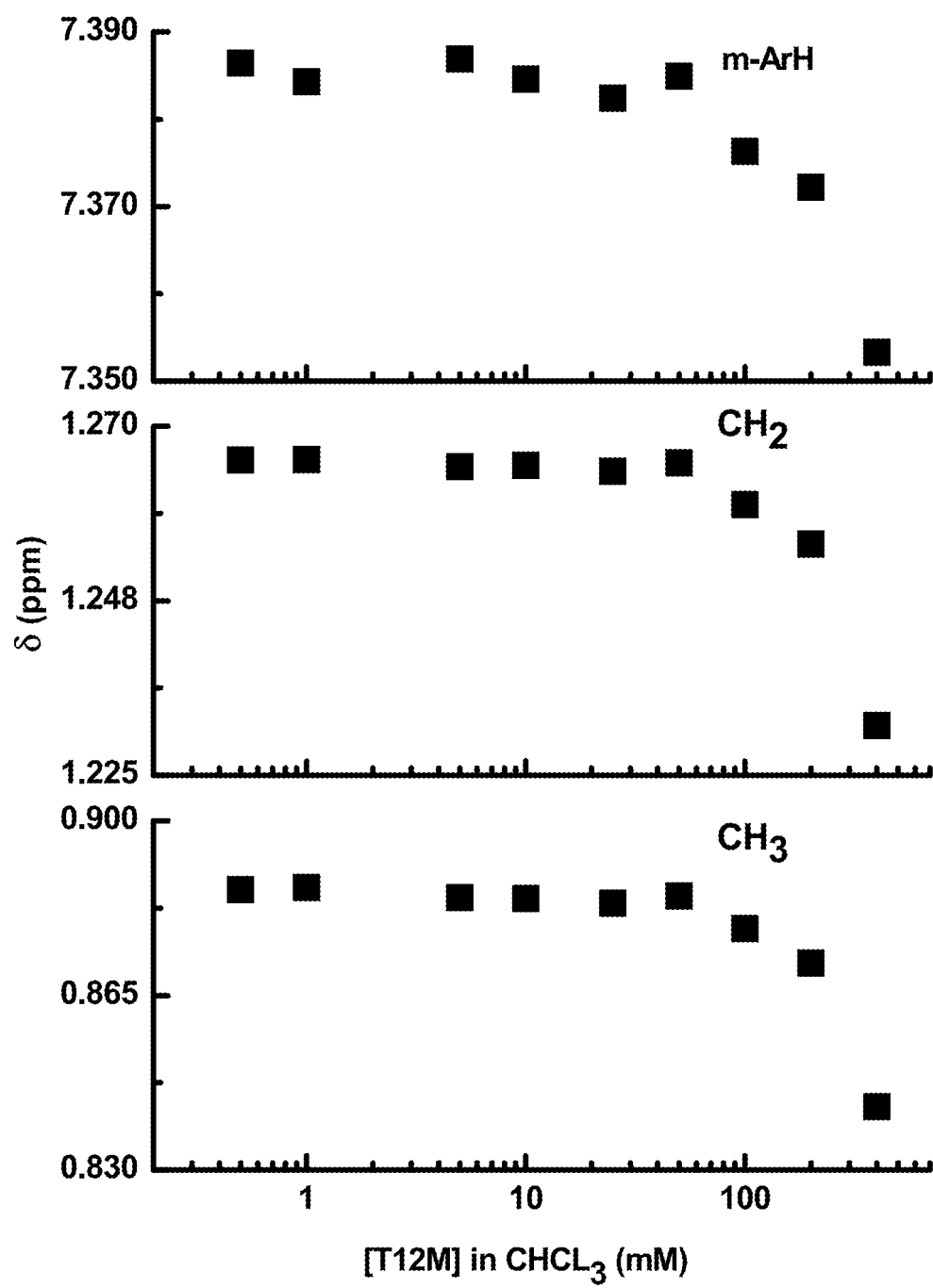
FIG. 9 shows the chemical shift values (ppm) of various groups of T12M as a function of concentration in $CDCl_3$.
Figure 10:
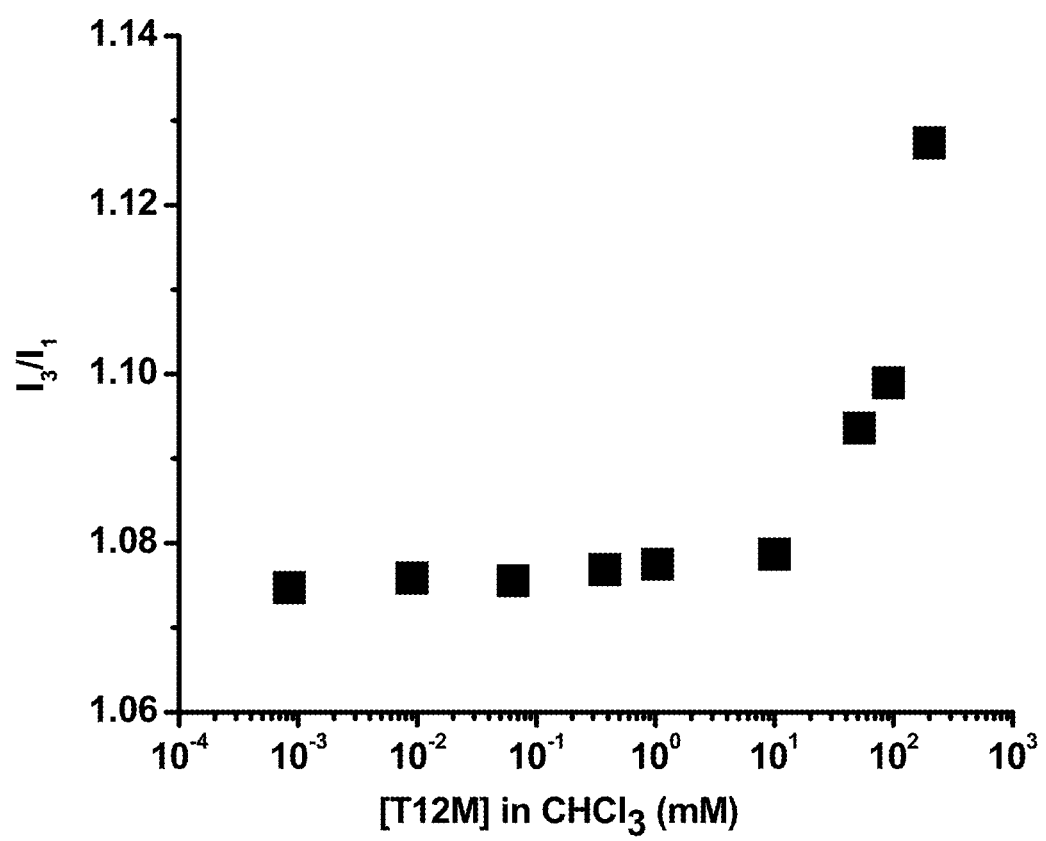
FIG. 10 is a plot of $I_1/I_3$ ratios of pyrene fluorescence quenching for T12M in $CHCl_3$.

In a non-aqueous solvent, chloroform, T12M formed reverse micelles. The CMC of T12M in chloroform, determined from $^1$H NMR (FIG. 9), was ~37 mM; that from fluorescence quenching experiments with pyrene (FIG. 10) was ~10 mM. The value determined from $^1$H NMR was probably an overestimate because of dominant changes in ppm values of protons due to ring current effect of the aromatic groups of MBA, as explained in Example 4. The scattering intensity of reverse micelles of T12M in chloroform was too low to get meaningful results from DLS.

Example 4. Structural Analysis from NMR and Computational Studies

Computational Methods: The conformation of T12M was generated utilizing the conformational search with CONFLEX program. Since CONFLEX program does not handle the ionic species properly, a molecular model of diacetyl-L-tartaric acid was input into the CONFLEX program and a conformational search was undertaken using MMFF94S molecular mechanics force field. The 115 conformers obtained within 7 kcal/mol were further optimized at B3LYP/aug-cc-pVDZ/PCM level. The minimum energy conformer determined in this manner was used to fix the structure of the head group and to build the structure of T12M by replacing the H of one COOH group with MBA and attaching dodecyl alkyl chain to the other carboxylic group. The placement of MBA and the long chain was based on the results from 2D ROESY and 1H-NMR experiments. The length of hydrophobic chain determined from Tanford equation, as described in Example 2, was set at 16.68 Å.

Figure 11:
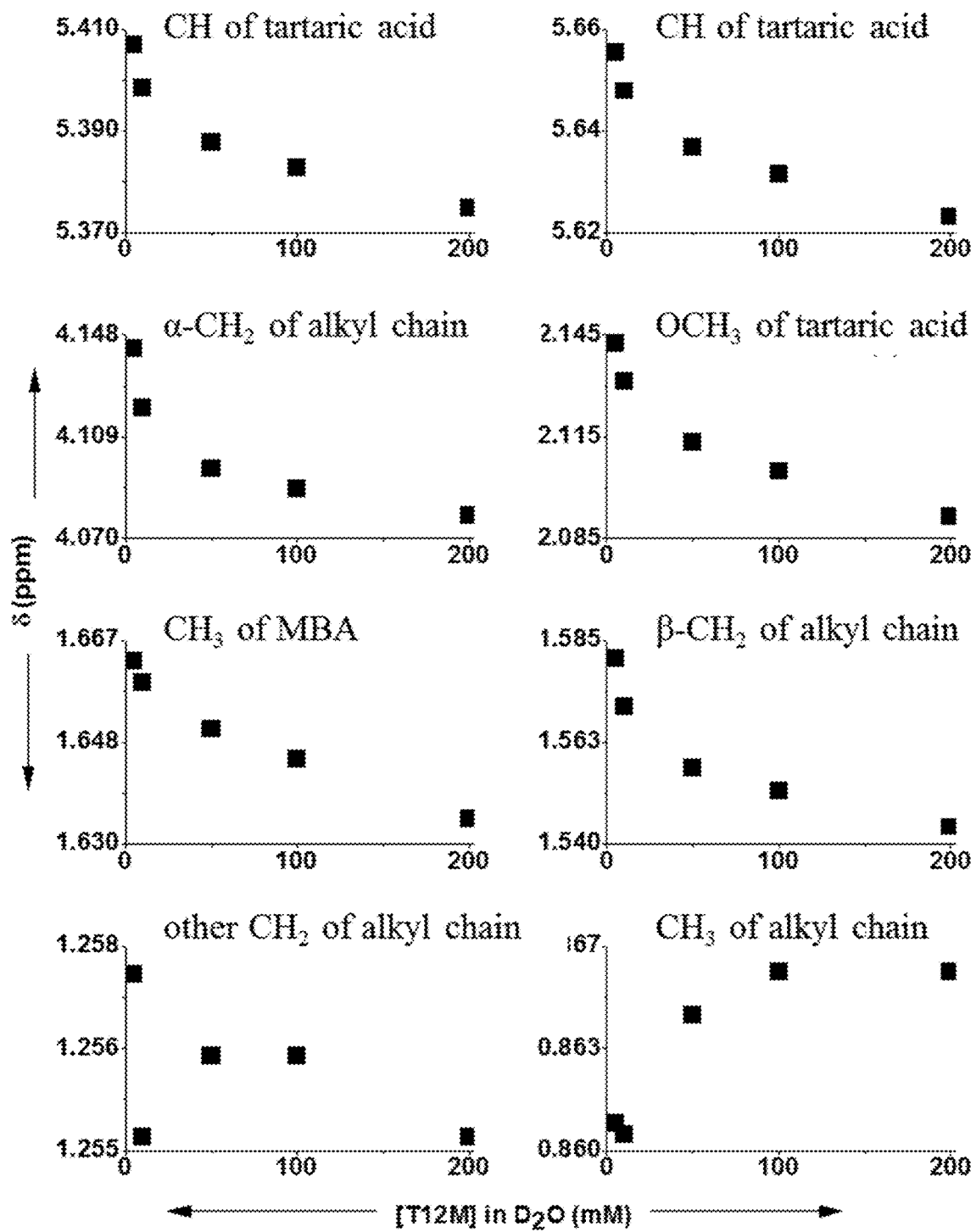
FIG. 11 shows the chemical shift (δ) values of 200 mM T12M in $D_2O$ from $^1$H NMR spectra showing proton peaks for: CH of tartaric acid, α-$CH_2$ of alkyl chain, $OCH_3$ of tartaric acid, $CH_3$ of MBA, β-$CH_2$ of alkyl chain, other $CH_2$ of alkyl chain and $CH_3$ of alkyl chain.

2D-ROESY data and the ring current effect associated with aromatic group was used previously to determine the architecture of micelles and biomembranes. The ring current associated with the phenyl ring of MBA can shield or deshield neighboring protons through space causing respective up-field or down-field chemical shift values (δ), thereby revealing the conformation of the surfactants in micelles. The ring current effect is governed by Equation 6.

$$\delta_{rc} = iB(1-3\cos^2\theta)/r^3 \quad (6)$$

where i is a ring-current factor, B is the constant of proportionality, θ is the angle (between aromatic electron cloud and proton), and r is the distance (from aromatic ring to proton). The chemical shifts for methine (CH) and acetyl (OAc) protons of tartaric acid and for α-$CH_2$ and β-$CH_2$ protons of alkyl chain (FIG. 11 and FIG. 14.) of T12M progressively shifted up-field with increases in concentration from 5-200 mM indicating that these protons are in close proximity to MBA and in the shielded region. Only the methyl group protons of the alkyl chain showed downfield δ (FIG. 11) indicating presence in the de-shielded region of MBA. It was conceivable that the methylene protons adjacent to methyl protons of the alkyl chain may be present in the deshielded region of MBA, however, the methylene protons adjacent to the α-$CH_2$ protons of the alkyl chain were expected be present the shielded region of MBA. The presence of some $CH_2$ protons of the alkyl chain in the shielded and some in the deshielded regions of MBA resulted in overall line broadening (FIG. 14) and random changes in their chemical shift values (δ) with concentration (FIG. 11G).

Figure 12A:
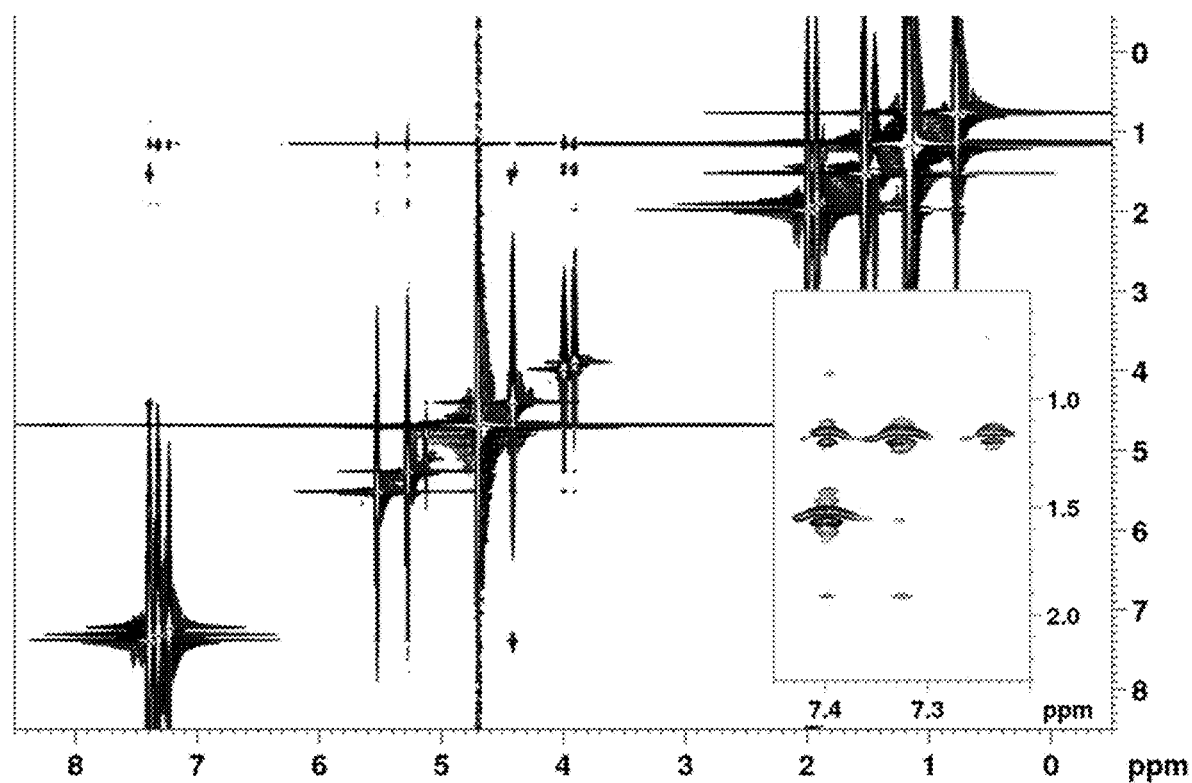
FIGS. 12A-12B are $^1$H-$^1$H 2D ROESY spectra of 200 mM T12M in $D_2O$ (FIG. 12A) and $CDCl_3$ (FIG. 12B). Insets show the expanded view of cross correlation peaks from 7.2-7.45 ppm.

The 2D $^1H$-$^1H$ ROESY NMR (FIG. 12A) of a 200 mM T12M solution showed cross peaks corresponding to MBA and all protons of T12M indicating that all protons of MBA and T12M in the aggregate at 200 mM are within the distance of 5-6 Å. In other words, the proximity of the aromatic protons of MBA and the alkyl chain protons of T12M, including the methyl protons, as determined by ring current effects was supported by 2D ROESY experiments (FIG. 12A). The protons of the methyl groups of the alkyl chain of T12M would only come in proximity of the MBA in 2 possible ways: (a) when the alkyl chain of T12M loops around; or (b) when the aggregates are interdigitated. The large up-field shift of methyl groups in the alkyl chain of T12M and the results from 2D experiments were only supported by option (b) as it would be impossible for the majority of the alkyl chain of T12M to loop around. Option (b) also corroborated the X-ray data.

Figure 12B:
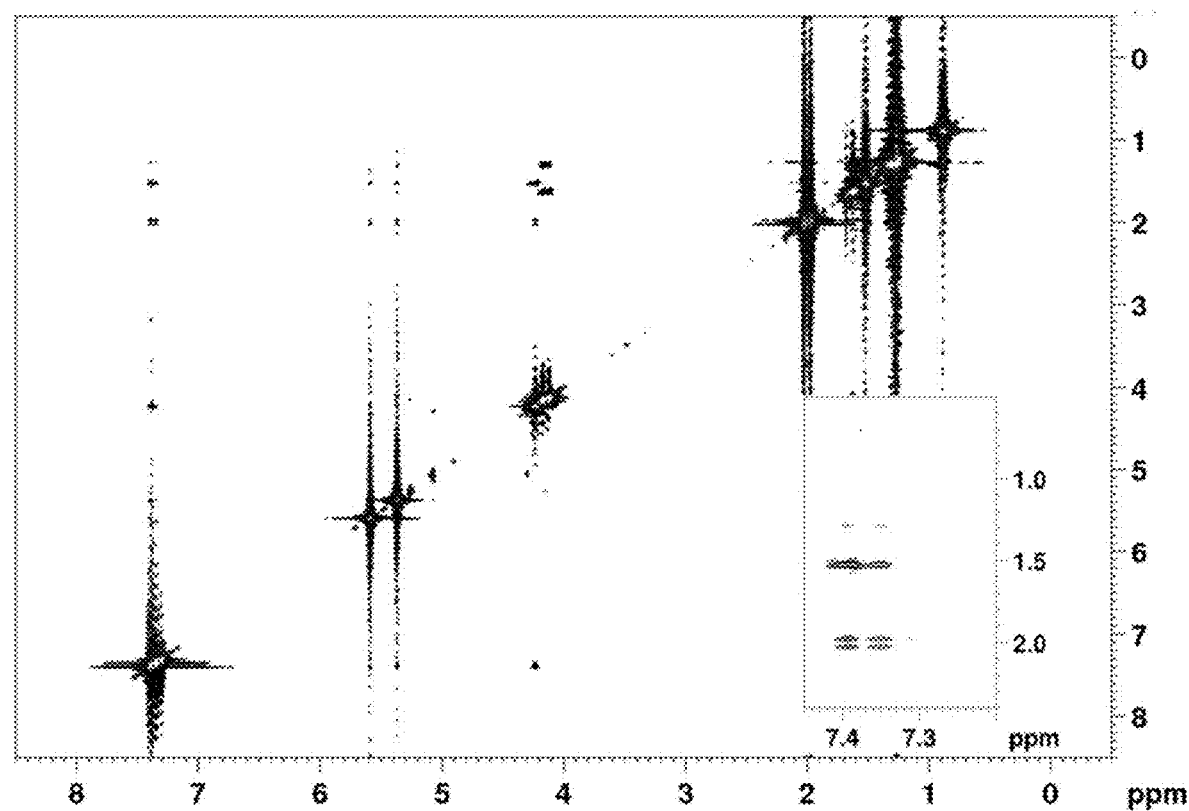

2D $^1H$-$^1H$ ROESY NMR experiments of T12M in $CDCl_3$ (FIG. 12B) did not show cross peaks corresponding to MBA and the methyl protons in alkyl chain of T12M, which indicated that the protons of methyl group and aromatic protons of MBA were far away from each other. The methyl protons in the alkyl chain of T12M can only be far away from MBA when they (a) don't form micelles or (b) when they form reverse micelles. Data from chemical shift values (ppm) of various groups of T12M as a function of concentration in $CDCl_3$ (FIG. 9) and pyrene fluorescence quenching for T12M in $CHCl_3$ (FIG. 10) indicated the formation of reverse micelles in chloroform. Thus, it may be inferred that 2D $^1H$-$^1H$ ROESY NMR experiments of T12M in $CDCl_3$ supported the presence of reverse micelles.

Figure 13:
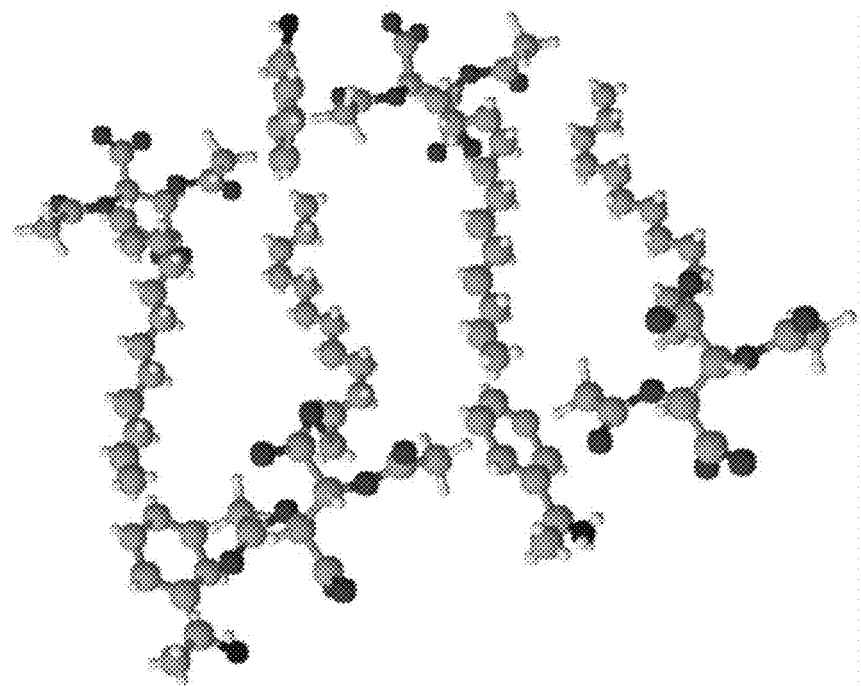
FIG. 13 is a rendering of the micellar arrangement for 200 mM T12M in water.
Figure 14A:
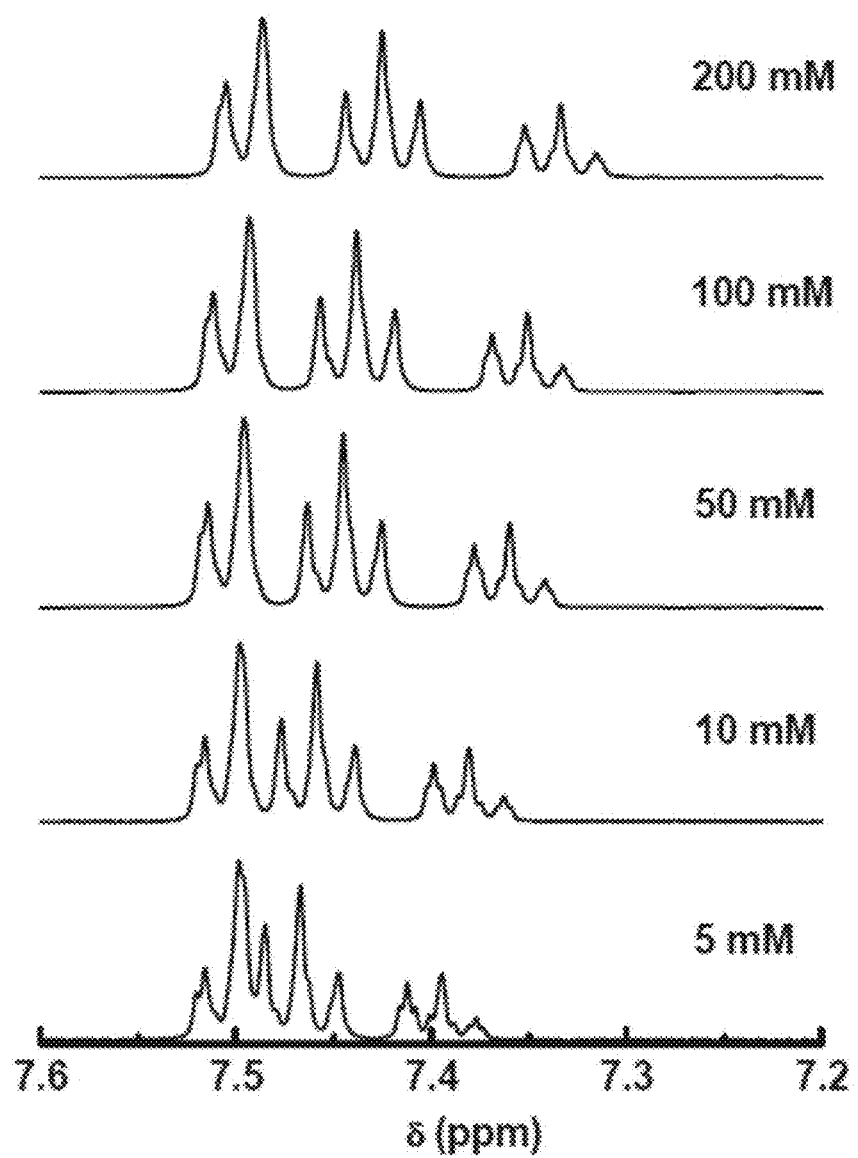
FIGS. 14A-14F are 1H NMR spectra of 200 mM T12M in $D_2O$ showing proton peaks of ArH of MBA (FIG. 14A), CH of tartaric acid (FIG. 14B), α-CH$_2$ of side chain (FIG. 14C), OCH$_3$ of tartaric acid (FIG. 14D), CH$_3$ of MBA (FIG. 14E), and B—CH$_2$ of side chain (FIG. 14F).
Figure 14B:
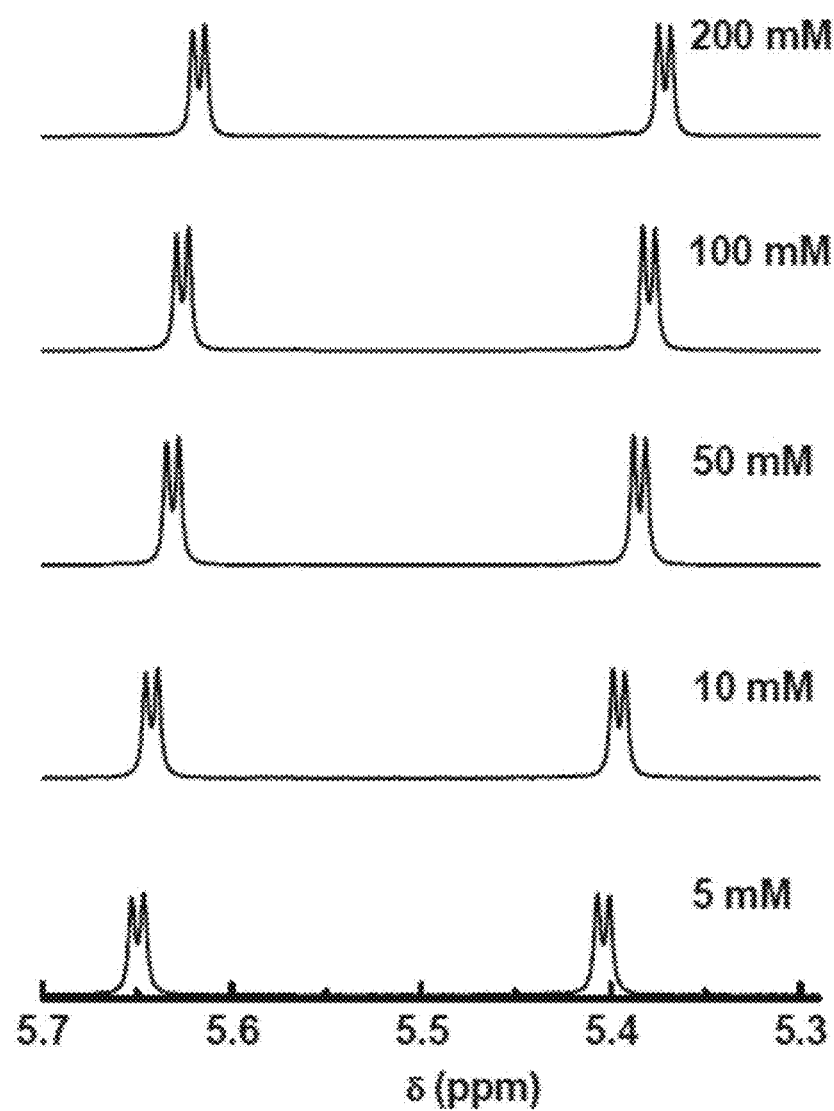
Figure 14C:
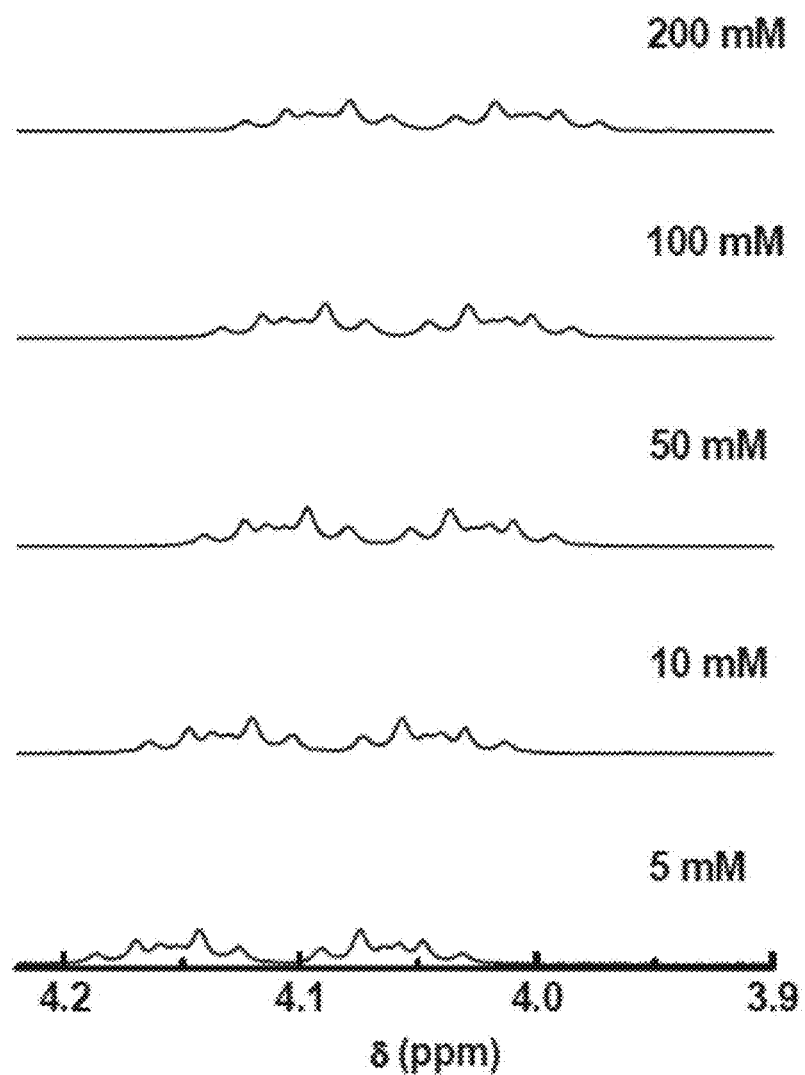
Figure 14D:
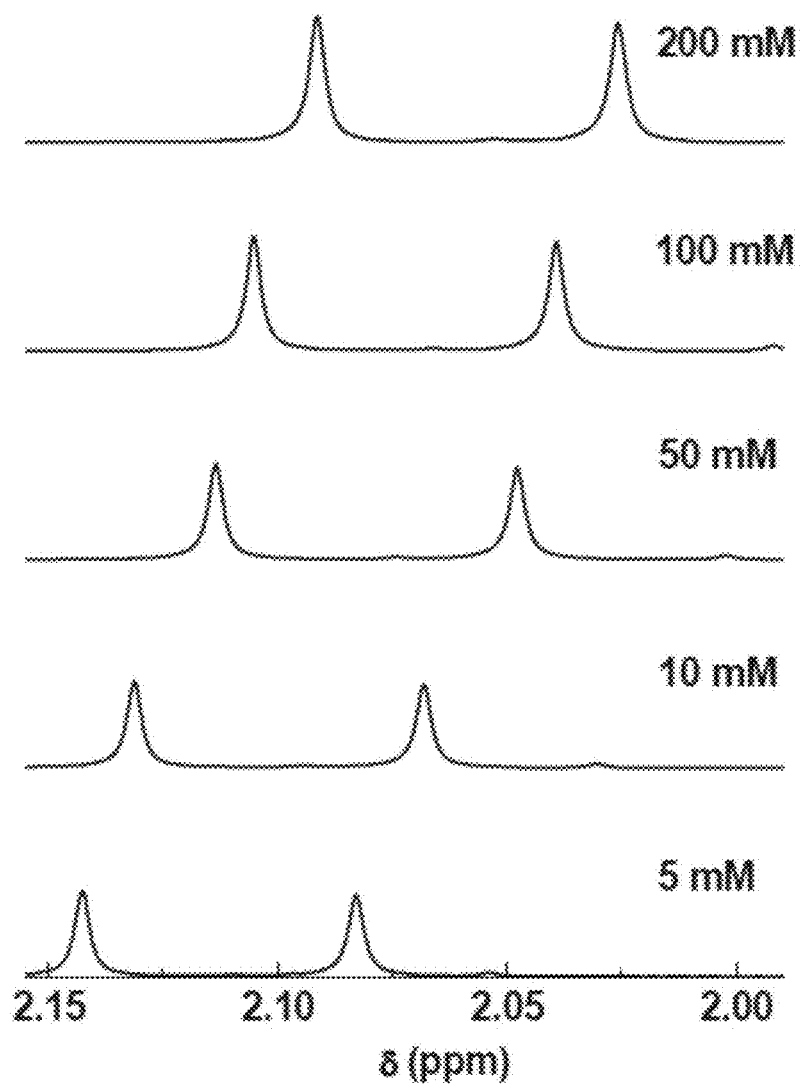
Figure 14E:
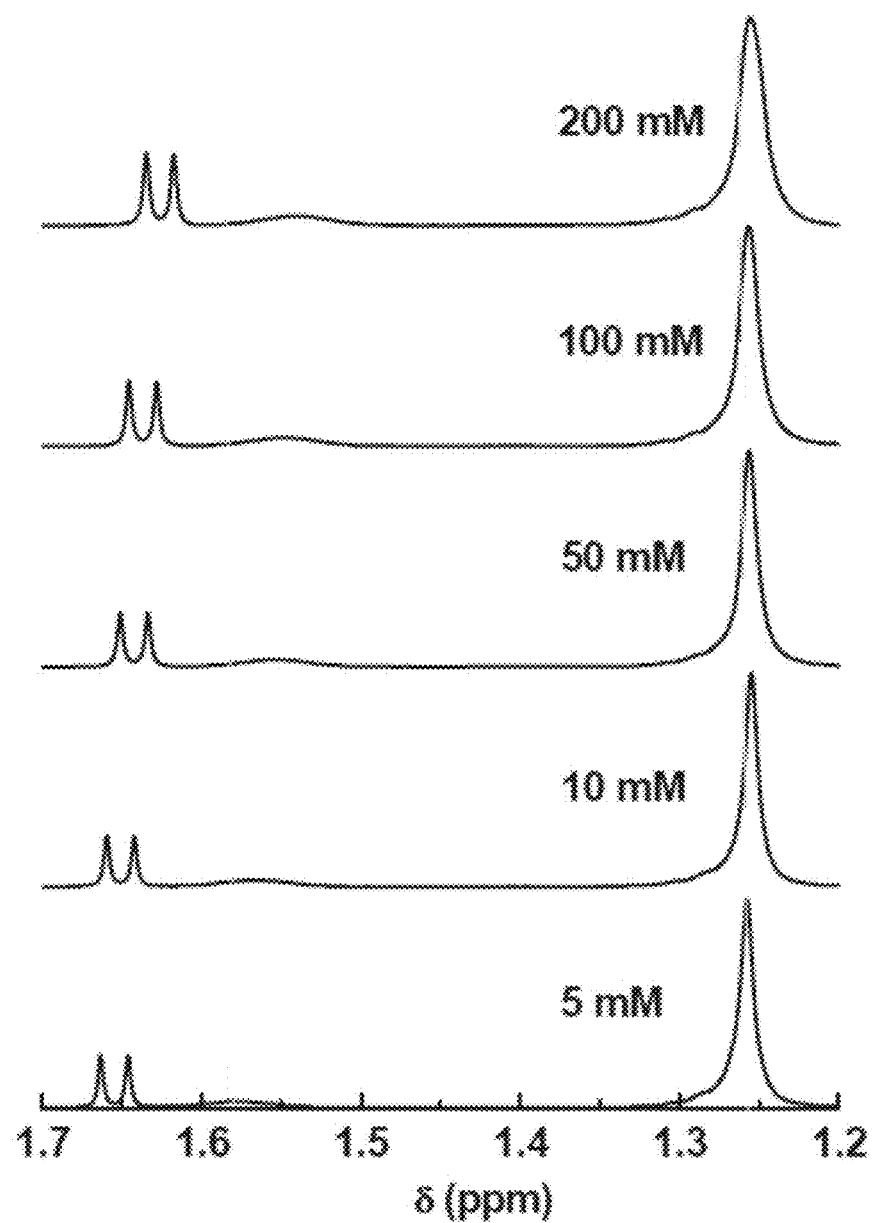
Figure 14F:
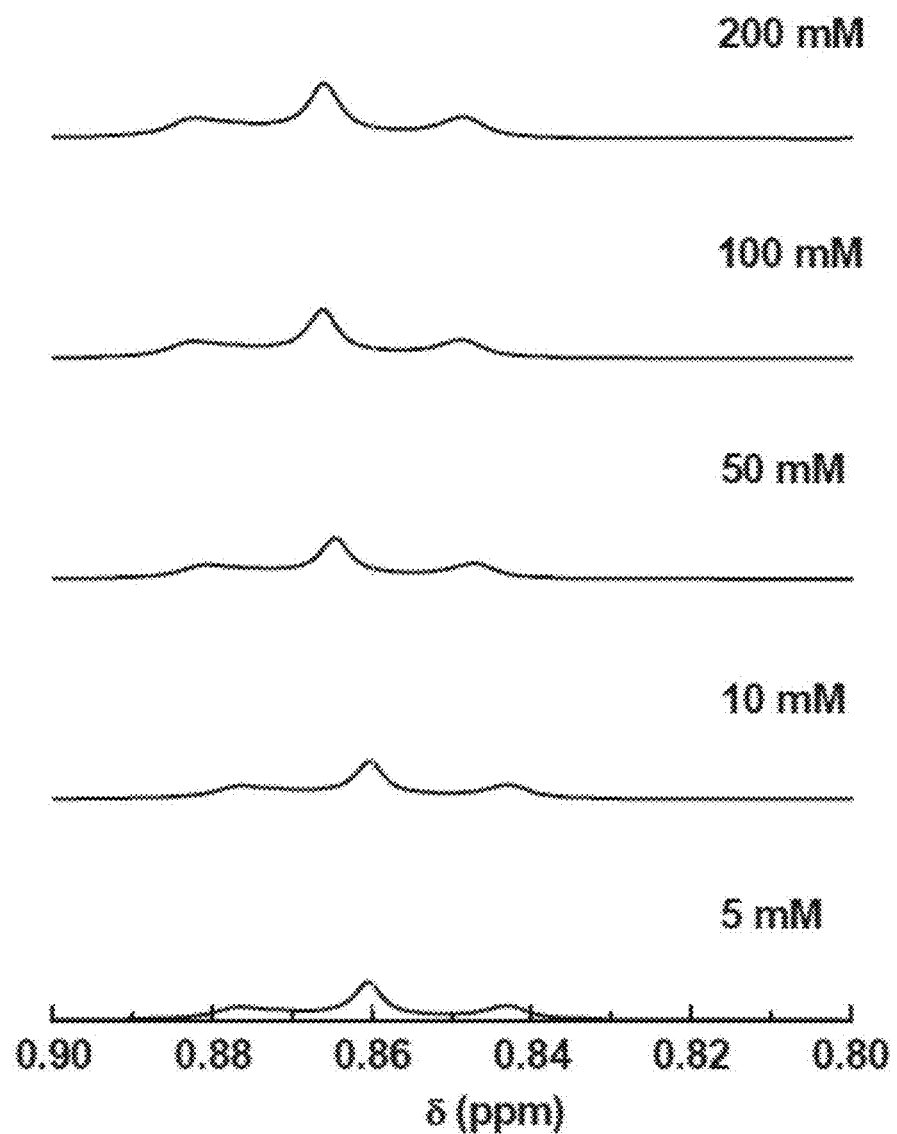

One of the most important results from the NMR experiments is the progressive change in δ of protons with increase in concentration of T12M (FIG. 11) which indicated an increase in the packing density of micelles. The extent of change in δ was highest between 5 and 10 mM and relatively less between 100 and 200 mM. This observation indicated that spherical/rod like micelles at ~10-50 mM had a more compact arrangement than lamellar structures at 200 mM. The arrangement for CMAs of T12M at 200 mM, consistent with all of the experimental data is depicted in FIG. 13. This rendering demonstrates why almost all protons of T12M were in the shielded or de-shielded region.

While several embodiments of the present invention have been described and illustrated herein, it is to be understood that the foregoing embodiments are presented by way of example only and that, within the scope of the appended claims and equivalents thereto, the invention may be practiced otherwise than as specifically described and claimed.

For reasons of completeness, various aspects of the invention are set out in the following numbered clauses:

Clause 1. A compound of formula (I)

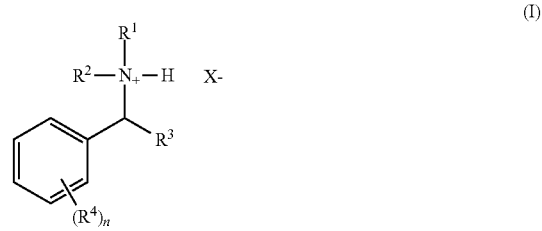

wherein
X— has formula (II)

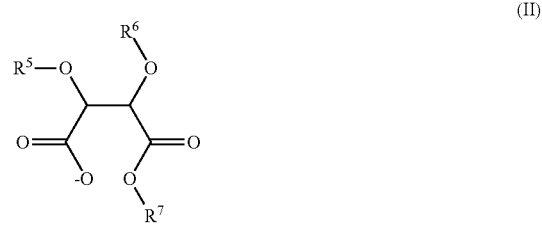

$R^1$ and $R^2$ are each independently hydrogen, $C_{1-4}$alkyl, $C_{3-4}$cycloalkyl, or —$CH_2$-cyclopropyl; or $R^1$ and $R^2$, taken together with the nitrogen to which they attach form a 4- to 7-membered saturated heterocycle;

$R^3$ is hydrogen, $C_{1-4}$alkyl, $C_{1-4}$haloalkyl, $C_{3-4}$cycloalkyl, —$CH_2$-cyclopropyl, or —$CH_2$—OH;

$R^4$ is halogen, cyano, $C_{1-4}$alkyl, $C_{1-4}$haloalkyl, OH, —$OC_{1-4}$alkyl, or —$OC_{1-4}$haloalkyl; wherein optionally two alkyl groups, taken together with the carbon atoms to which they attach form a 5- to 7-membered carbocyclic ring;

n is 0, 1, 2, 3, 4, or 5;

$R^5$ and $R^6$ are each independently hydrogen, —$C(O)C_{1-4}$alkyl, —$C(O)C_{3-4}$cycloalkyl, —$C(O)$—$CH_2$— cyclopropyl, $C_{1-4}$alkyl, or $C_{1-4}$haloalkyl; and $R^7$ is $C_{6-18}$alkyl optionally substituted with 1-6 halogen.

Clause 2. The compound of clause 1, wherein $R^1$ is hydrogen.

Clause 3. The compound of clause 1 or 2, wherein $R^2$ is hydrogen.

Clause 4. The compound of any of clauses 1-3, wherein $R^3$ is $C_{1-4}$alkyl.

Clause 5. The compound of clause 4, wherein $R^3$ is $CH_3$.

Clause 6. The compound of any of clauses 1-5, wherein n is 0.

Clause 7. The compound of any of clauses 1-6, wherein $R^5$ is —$C(O)C_{1-4}$alkyl.

Clause 8. The compound of clause 7, wherein $R^5$ is —$C(O)CH_3$.

Clause 9. The compound of any of clauses 1-8, wherein $R^6$ is —$C(O)C_{1-4}$alkyl.

Clause 10. The compound of clause 9, wherein $R^6$ is —$C(O)CH_3$.

Clause 11. The compound of any of clauses 1-10, wherein $R^7$ is $C_{12}$alkyl.

Clause 12. The compound of any of clauses 1-10, wherein $R^7$ is straight chain $C_{12}$alkyl.

Clause 13. The compound of any of clauses 1-12, wherein the compound of formula (I) has formula (I-a)

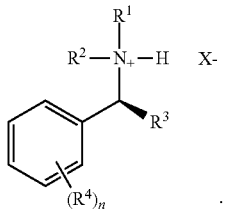

(I-a)

Clause 14. The compound of any of clauses 1-12, wherein the compound of formula (I) has formula (I-b)

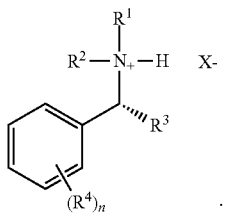

(I-b)

Clause 15. The compound of any of clauses 1-14, wherein formula (II) is formula (II-a)

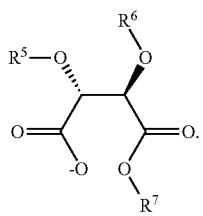

(II-a)

Clause 16. An ionic liquid comprising a plurality of compounds of any of clauses 1-15.

Clause 17. A composition comprising the compound of any of clauses 1-15.

Clause 18. The composition of clause 17 further comprising an aqueous medium, wherein the compound has a critical micelle concentration of about 0.0001-0.0005 M in the aqueous medium.

Clause 19. The composition of clause 17 further comprising a micellar aggregate, the micellar aggregate comprising a plurality of compounds of any of claims 1-15.

Clause 20. The composition of clause 19, wherein the micellar aggregate comprises a spherical micelle, a rod-like micelle, and/or a lamellar structure.

Clause 21. The composition of clause 17 further comprising an organic medium, wherein the compound has a critical micelle concentration of about 0.003-0.1 M in the organic medium.

Clause 22. The composition of clause 17 further comprising a reverse micellar aggregate, the reverse micellar aggregate comprising a plurality of the compound of any of claims 1-15.

What is claimed is:

1. A salt of formula (I)

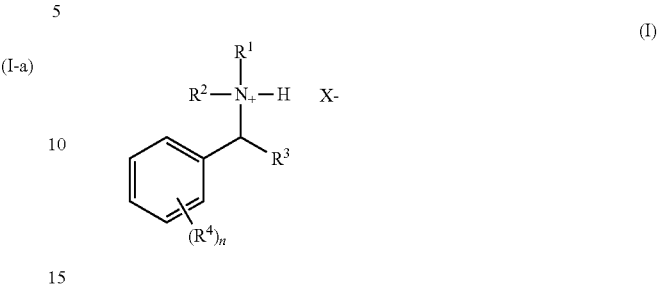

(I)

wherein

X— has formula (II)

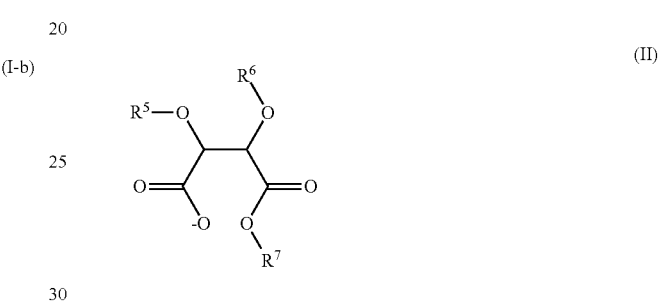

(II)

$R^1$ and $R^2$ are each independently hydrogen, $C_{1-4}$alkyl, $C_{3-4}$cycloalkyl, or —CH$_2$-cyclopropyl; or $R^1$ and $R^2$, taken together with the nitrogen to which they attach form a 4- to 7-membered saturated heterocycle;

$R^3$ is hydrogen, $C_{1-4}$alkyl, $C_{1-4}$haloalkyl, $C_{3-4}$cycloalkyl, —CH$_2$-cyclopropyl, or —CH$_2$—OH;

$R^4$ is halogen, cyano, $C_{1-4}$alkyl, $C_{1-4}$haloalkyl, OH, —OC$_{1-4}$alkyl, or —OC$_{1-4}$haloalkyl; wherein optionally two alkyl groups, taken together with the carbon atoms to which they attach form a 5- to 7-membered carbocyclic ring;

n is 0, 1, 2, 3, 4, or 5;

$R^5$ and $R^6$ are each independently hydrogen, —C(O)C$_{1-4}$alkyl, —C(O)C$_{3-4}$cycloalkyl, —C(O)—CH$_2$-cyclopropyl, $C_{1-4}$alkyl, or $C_{1-4}$haloalkyl; and $R^7$ is $C_{6-18}$alkyl optionally substituted with 1-6 halogen.

2. The salt of claim 1, wherein $R^1$ is hydrogen.

3. The salt of claim 2, wherein $R^2$ is hydrogen.

4. The salt of claim 3, wherein $R^3$ is $C_{1-4}$alkyl.

5. The salt of claim 4, wherein $R^3$ is CH$_3$.

6. The salt of claim 3, wherein n is 0.

7. The salt of claim 3, wherein $R^5$ is —C(O)C$_{1-4}$alkyl.

8. The salt of claim 7, wherein $R^5$ is —C(O)CH$_3$.

9. The salt of claim 7, wherein $R^6$ is —C(O)C$_{1-4}$alkyl.

10. The salt of claim 9, wherein $R^6$ is —C(O)CH$_3$.

11. The salt of claim 3, wherein $R^7$ is $C_{12}$alkyl.

12. The salt of claim 11, wherein $R^7$ is straight chain $C_{12}$alkyl.

13. The salt of claim 1, wherein the salt of formula (I) has formula (I-a)

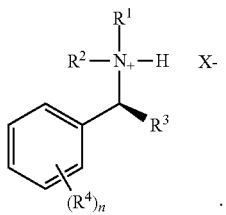

14. The salt of claim 1, wherein the salt of formula (I) has formula (I-b)

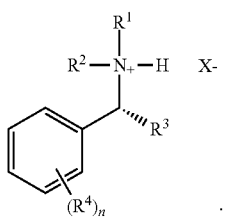

15. The salt of claim 1, wherein formula (II) is formula (II-a)

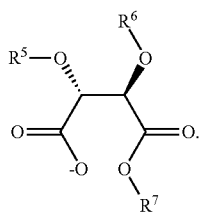

16. An ionic liquid comprising the salt of claim 1.
17. A composition comprising the salt of claim 1.
18. The composition of claim 17 further comprising an aqueous medium, wherein the salt has a critical micelle concentration of about 0.0001-0.0005 M in the aqueous medium.
19. The composition of claim 17 further comprising a micellar aggregate, the micellar aggregate comprising the salt.
20. The composition of claim 19, wherein the micellar aggregate comprises a spherical micelle, a rod-like micelle, and/or a lamellar structure.
21. The composition of claim 17 further comprising an organic medium, wherein the salt has a critical micelle concentration of about 0.003-0.1 M in the organic medium.
22. The composition of claim 17 further comprising a reverse micellar aggregate, the reverse micellar aggregate comprising the salt.
23. The composition of claim 19, wherein the micellar aggregate contains an aggregation number of salt greater than 50.
24. The salt of claim 1 of the following formula

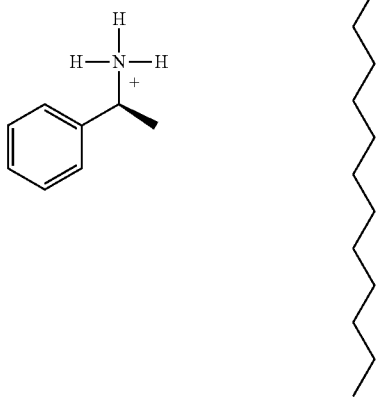

25. The ionic liquid of claim 16, wherein the monoalkylester from tartaric acid formula (II) is the monoalkylester from D-tartaric.

* * * * *